(12) United States Patent
Min et al.

(10) Patent No.: US 9,717,914 B2
(45) Date of Patent: Aug. 1, 2017

(54) USE OF CARDIOHEMIC VIBRATION FOR PACING THERAPIES

(75) Inventors: Xiaoyi Min, Thousand Oaks, CA (US);
Gene A. Bornzin, Simi Valley, CA (US); Jay Snell, Studio City, CA (US); Josh Reiss, Kirkland, WA (US)

(73) Assignee: Pacesetter, Inc., Sylmar, CA (US)

( * ) Notice: Subject to any disclaimer, the term of this patent is extended or adjusted under 35 U.S.C. 154(b) by 1408 days.

(21) Appl. No.: 12/211,760

(22) Filed: Sep. 16, 2008

(65) Prior Publication Data
US 2010/0069768 A1 Mar. 18, 2010

(51) Int. Cl.
*A61N 1/36* (2006.01)
*A61N 1/365* (2006.01)
*A61N 1/362* (2006.01)
*A61B 5/0215* (2006.01)
*A61B 5/026* (2006.01)
*A61B 7/02* (2006.01)
*A61B 8/08* (2006.01)

(52) U.S. Cl.
CPC ........... *A61N 1/365* (2013.01); *A61N 1/3627* (2013.01); *A61B 5/026* (2013.01); *A61B 5/0215* (2013.01); *A61B 7/023* (2013.01); *A61B 8/08* (2013.01); *A61B 2562/0219* (2013.01); *A61N 1/36578* (2013.01)

(58) Field of Classification Search
CPC ........ A61N 1/056; A61N 1/36; A61N 1/3605; A61N 1/36114; A61N 1/3627; A61N 1/365; A61N 1/36571; A61N 1/3682; A61N 8/06; A61B 5/026; A61B 8/02

USPC ............... 600/508, 509, 528, 586; 607/9, 17
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,940,052 A | 7/1990 | Mann et al. | |
| 4,944,298 A | 7/1990 | Sholder | |
| 4,989,611 A * | 2/1991 | Zanetti et al. | 600/508 |
| 5,466,254 A | 11/1995 | Helland | |
| 5,476,483 A | 12/1995 | Bornzin et al. | |
| 6,314,323 B1 | 11/2001 | Ekwall | |
| 7,139,609 B1 * | 11/2006 | Min | A61B 5/02 600/528 |
| 7,676,266 B1 * | 3/2010 | Kroll | 607/18 |
| 2003/0055345 A1 | 3/2003 | Eigler et al. | |
| 2006/0178586 A1 * | 8/2006 | Dobak, III | A61B 5/02 600/508 |
| 2008/0228094 A1 * | 9/2008 | Audet et al. | 600/513 |
| 2009/0192561 A1 * | 7/2009 | Bauer | A61N 1/36585 607/18 |

OTHER PUBLICATIONS

Gibson, Derek G. et al., "Clinical Assessment of Left Ventricular Diastolic Function," Heart. 2003;89:231-238.

(Continued)

*Primary Examiner* — Amanda Patton

(57) ABSTRACT

An exemplary method includes receiving a signal from an intrathoracic vibration sensor, analyzing the signal for vibration associated with deceleration of blood flow into the left ventricle, based at least in part on the analyzing, deciding whether to call for adjustment to one or more parameters of a bi-ventricular pacing therapy. Other exemplary methods, devices, systems, etc., are also disclosed.

16 Claims, 15 Drawing Sheets

(56) References Cited

OTHER PUBLICATIONS

Hofmann, Thomas MD et al., "Simultaneous Measurement of Pulmonary Venous Flow by Intravascular Catheter Doppler Velocimetry and Transesophageal Doppler Echocardiography: Relation to Left Atrial Pressure and Left Atrial and Left Ventricular Function," J Am Coll Cardiol. 1995;26:239-249.
Manson, Abigail L. et al., "Relationship of the Third Heart Sound to Transmitral Flow Velocity Deceleration," Circulation. 1995;92:388-394.
Rivas-Gotz, Carlos MD et al., "Time Interval Betwen Onset of Mitral Inflow and Onset of Early Diastolic Velocity by Tissue Doppler: A Novel Index of Left Ventricular Relaxation," J Am Coll Cardiol. 2003;42(8):1463-1470.
Shioi, Tetsuo MD et al., "Tapamycin Attenuates Load-Induced Cardiac Hypertrophy in Mice," Circulation. 2003;107:1664-1670.
Tanner, Hildegard et al., "The prevalence of anemia in chronic heart failure," International Journal of Cardiology. 2002;86:115-121.

* cited by examiner

Exemplary Plots 700

USE OF CARDIOHEMIC VIBRATION FOR PACING THERAPIES

TECHNICAL FIELD

Subject matter presented herein generally relates to sensing cardiohemic vibration for pacing therapies.

BACKGROUND

Gibson and Francis recently reported that "diastolic left ventricular disease is being increasingly incriminated as a cause of limitation of exercise tolerance, whether or not ejection fraction is normal, though the mechanisms by which it does so are far from clear" and that "it has been suggested that no diastolic abnormality at all need be demonstrated for a diagnosis of possible or probable diastolic heart failure to be made" ("Clinical Assessment of Left Ventricular Diastolic Function," *Heart* 2003; 89:231-238).

As noted by Gibson and Francis, left ventricular diastole involves both muscle mechanics and fluid mechanics. Such mechanisms may include decline of the myocardial active state following systole, passive effects of connective tissue (compression or extension of connective tissue may store potential energy from systole and release it in early diastole and, in late diastole, properties of connective tissue may determine ventricular compliance), rapid changes in atrial and ventricular pressures, transmitral flow, interactions from right ventricle and pericardium, and atrial systole. Further, such mechanisms may be interrelated, for example, a fluid pressure may facilitate muscle contraction.

In a clinical setting, a care provider may measure many parameters in an effort to determine whether a patient suffers from diastolic heart failure whereas a typical implantable device lacks resources to perform adequate measurements and make robust determinations. Consequently, a need exists for measurement and determination techniques that can allow an implantable device to diagnose diastolic left ventricular disease.

As described herein, various techniques rely on parameters that relate to muscle mechanics and/or fluid mechanics to detect conditions that may be associated with diastolic heart failure.

SUMMARY

An exemplary method includes receiving a signal from an intrathoracic vibration sensor, analyzing the signal for vibration associated with deceleration of blood flow into the left ventricle, based at least in part on the analyzing, deciding whether to call for adjustment to one or more parameters of a bi-ventricular pacing therapy. Other exemplary methods, devices, systems, etc., are also disclosed.

In general, the various methods, devices, systems, etc., described herein, and equivalents thereof, are optionally suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims.

Exemplary Stimulation Device

The techniques described below are optionally implemented in connection with any stimulation device that is configured or configurable to stimulate and/or shock tissue.

Figure 1:
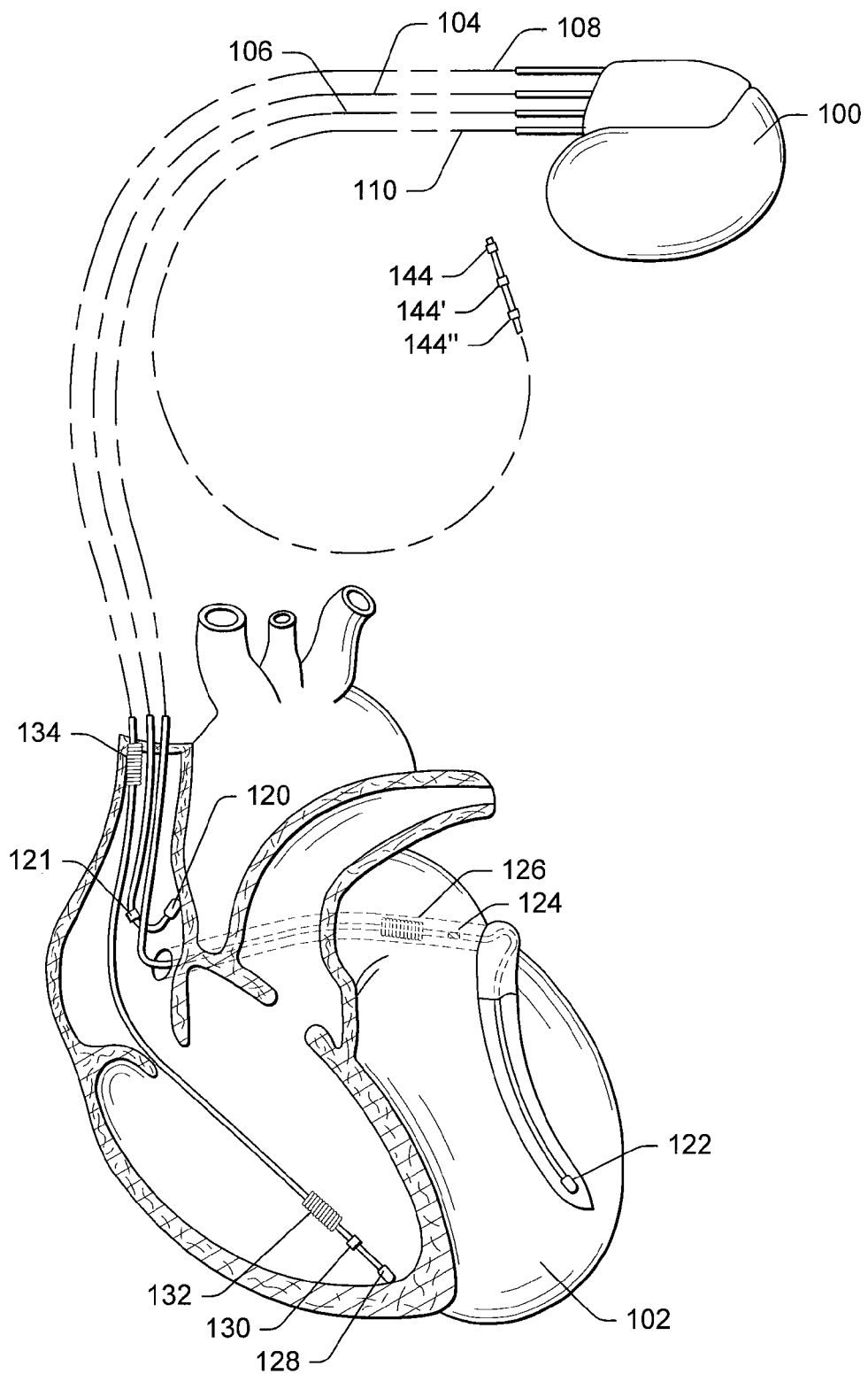
FIG. 1 is a simplified diagram illustrating an exemplary implantable stimulation device in electrical communication with at least three leads implanted into a patient's heart and at least one other lead for delivering stimulation and/or shock therapy.

FIG. 1 shows an exemplary stimulation device 100 in electrical communication with a patient's heart 102 by way of three leads 104, 106, 108, suitable for delivering multi-chamber stimulation and shock therapy. The device 100, as shown, may deliver cardiac resynchronization therapy (CRT). CRT provides an electrical solution to the symptoms and other difficulties brought on by heart failure (HF). CRT may deliver electrical impulses to the left ventricle and to the right ventricle, which is referred to as biventricular pacing.

Biventricular pacing aims to improve the efficiency of each contraction of the heart and the amount of blood pumped to the body, typically by improving left ventricular function. CRT can help lessen symptoms of HF and slow progression of HF.

Referring to FIG. 1, the leads 104, 106, 108 are optionally configurable for delivery of stimulation pulses suitable for stimulation of autonomic nerves, non-myocardial tissue, other nerves, etc. In addition, the device 100 includes a fourth lead 110 having, in this implementation, three electrodes 144, 144', 144" suitable for stimulation of autonomic nerves, non-myocardial tissue, other nerves, etc. For example, this lead may be positioned in and/or near a patient's heart or near an autonomic nerve within a patient's body and remote from the heart. In another example, the lead 110 includes an accelerometer or other mechanism for sensing vibrations of the heart (see, e.g., FIG. 10). While various examples refer to an accelerometer for sensing vibration, other sensors suitable for sensing vibration may be used.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves, non-myocardial tissue, other nerves, etc.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

Figure 2:
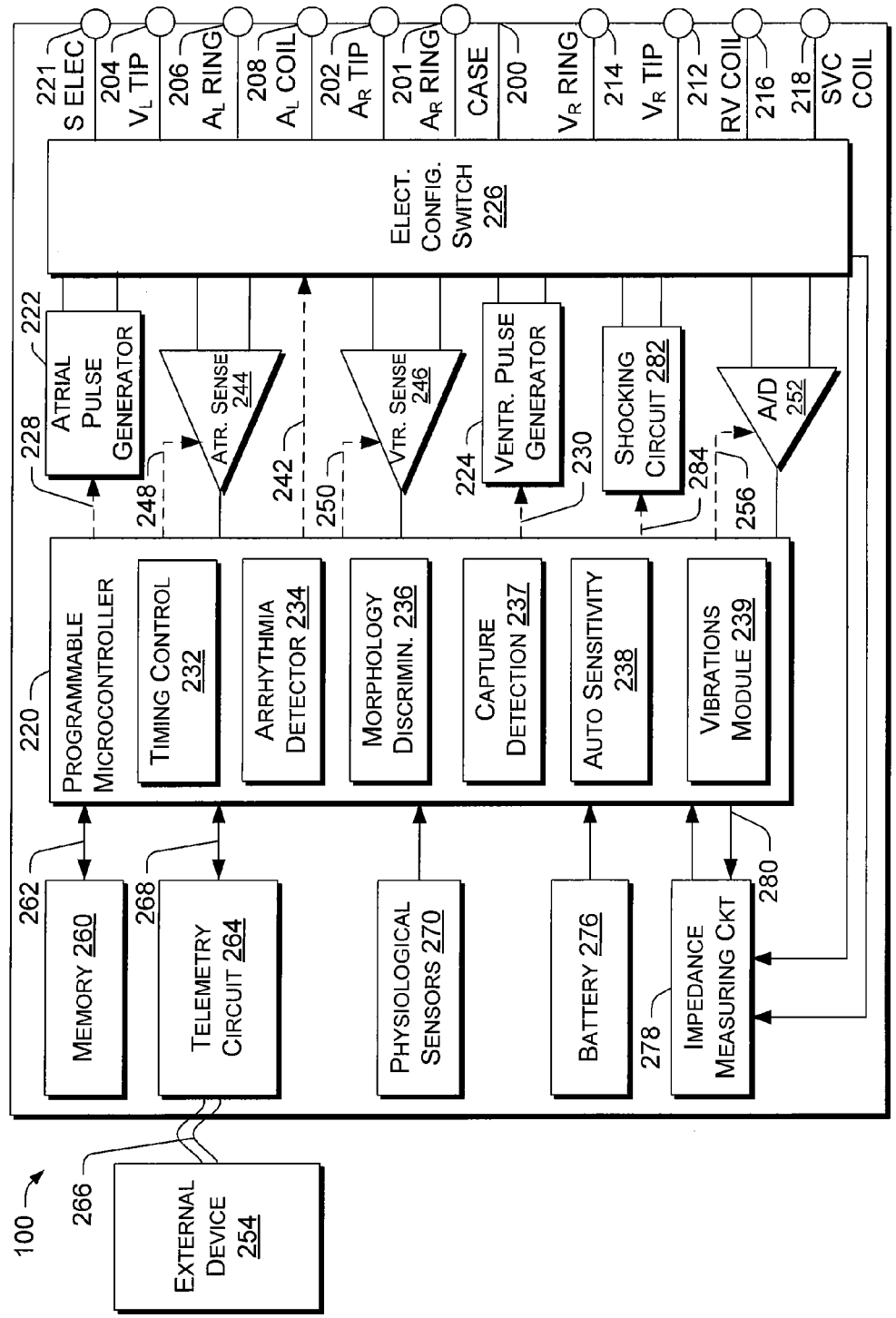
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and U.S. Pat. No. 4,944,298 (Sholder), all of which are incorporated by reference herein. For a more detailed description of the various timing intervals used within the stimulation device and their interrelationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology discrimination module 236, a capture detection module 237, a auto sensitivity module 238, a vibration sensing module 239 and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The vibration module 239 may perform a variety of tasks related to, for example, cardiohemic vibration information. This component can be utilized by the stimulation device 100 in determining therapy in response to vibration, a derivative thereof, and/or other parameter. The vibration module 239 may be implemented in hardware as part of the microcontroller 220, or as software/firmware instructions programmed into the device and executed on the microcontroller 220 during certain modes of operation. The vibration module 239 may optionally implement various exemplary methods described herein. The vibration module 239 may interact with the physiological sensors 270, the impedance measuring circuit 278 and optionally other modules.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals across any pair of desired electrodes. Where the lead 110 includes an accelerometer, then the accelerometer may output a signal that can be processed by the data acquisition system 252 or circuitry of the device 100.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

Pressure sensors for sensing left atrial pressure are discussed in U.S. Patent Application US2003/0055345 A1, to Eigler et al., which is incorporated by reference herein. The discussion pertains to a pressure transducer permanently implantable within the left atrium of the patient's heart and operable to generate electrical signals indicative of fluid pressures within the patient's left atrium. According to Eigler et al., the pressure transducer is connected to a flexible electrical lead, which is connected in turn to electrical circuitry, which includes digital circuitry for processing electrical signals. Noted positions of the transducer include within the left atrium, within a pulmonary vein, within the left atrial appendage and in the septal wall.

The exemplary device 100 optionally includes a connector capable of connecting a lead that includes a pressure sensor. For example, the connector 221 optionally connects to a pressure sensor capable of receiving information pertaining to chamber pressures or other pressures.

A study by Hofmann et al., "Simultaneous Measurement of Pulmonary Venous Flow by Intravascular Catheter Doppler Velocimetry and Transesophageal Doppler Echocardiography: Relation to Left Atrial Pressure and Left Atrial and Left Ventricular Function," *J Am Coll Cardiol.* 1995; 26(1): 239-249, used a "microtip" pressure transducer and noted that mean left atrial pressure was strongly correlated with the ratio of systolic to diastolic peak velocity, systolic velocity-time integral, time to maximal flow velocity and the ratio of systolic to diastolic flow duration. In particular, Hofmann et al. reported that the ratio of systolic to diastolic peak velocity and the time to maximal flow velocity were identified as strong independent predictors of mean left atrial pressure and that left atrial compliance was not found to be an independent predictor of mean left atrial pressure. This study indicates that surrogates may exist for indirect measurement or estimation of left atrial pressure or mean left atrial pressure.

Commercially available pressure transducers include those marketed by Millar Instruments (Houston, Tex.) under the mark MIKROTIP®. A study by Shioi et al., "Rapamycin Attenuates Load-induced Cardiac Hypertrophy in Mice," *Circulation* 2003; 107:1664-1670, measured left ventricular pressures in mice using a Millar pressure transducer inserted through the LV apex and secured in the LV apex with a purse-string suture using 5-0 silk. Various exemplary methods, devices, systems, etc., described herein optionally use such a pressure transducer to measure pressures in the body (e.g., chamber of heart, vessel, etc.).

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense pressure, respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device 100 optionally includes circuitry capable of sensing heart sounds and/or vibration associated with events that produce heart sounds. Such circuitry may include an accelerometer as conventionally used for patient position and/or activity determinations. Accelerometers typically include two or three sensors aligned along orthogonal axes. For example, a commercially available microelectromechanical system (MEMS) marketed as the ADXL202 by Analog Devices, Inc. (Norwood, Mass.) has a mass of about 5 grams and a 14 lead CERPAK (approx. 10 mm by 10 mm by 5 mm or a volume of approx. 500 mm$^3$). The ADXL202 MEMS is a dual-axis accelerometer on a single monolithic integrated circuit and includes polysilicon springs that provide a resistance against acceleration forces. The term MEMS has been defined generally as a system or device having micro-circuitry on a tiny silicon chip into which some mechanical device such as a mirror or a sensor has been manufactured. The aforementioned ADXL202 MEMS includes micro-circuitry and a mechanical oscillator.

Another commercially available MEMS accelerometer is the ADXL330 by Analog Devices, Inc., which is a small, thin, low power, complete three axis accelerometer with signal conditioned voltage outputs, all on a single monolithic IC. The ADXL330 product measures acceleration with a minimum full-scale range of ±3 g. It can measure the static acceleration of gravity in tilt-sensing applications, as well as dynamic acceleration resulting from motion, shock, or vibration. Bandwidths can be selected to suit the application, with a range of 0.5 Hz to 1,600 Hz for X and Y axes, and a range of 0.5 Hz to 550 Hz for the Z axis. Various heart sounds include frequency components lying in these ranges. The ADXL330 is available in a small, low-profile, 4 mm×4 mm×1.45 mm, 16-lead, plastic lead frame chip scale package (LFCSP_LQ).

For sensing vibration, a strain gauge may be used where vibrations emanating from the heart cause the strain gauge to deform. For example, a conventional type of strain gauge is formed of a thin film with a conductive wire or wires and associated terminals where tension causes an increase in resistance at the terminals and where compression decreases resistance at the terminals (e.g., a piezoresistive gauge). Vibrations may cause such a film to cycle between tension and compression and hence produce an oscillating signal as resistance changes. The oscillating signal may be analyzed to determine frequency of oscillation, which, in turn, can be an indicator of heart activity. A strain gauge may be configured to sense strain along a particular direction. Multiple strain gauges may be used to sense strain along different directions. A strain gauge may include tines to anchor the gauge to tissue or apertures for suturing the gauge to tissue.

A microphone may be used for sensing vibration. A conventional microphone includes a diaphragm and associated electronics that can alter a signal as energy impacts the diaphragm. Piezoelectric microphones rely on the ability of a material to produce a voltage when subject to pressure and to convert vibrations into an electrical signal. MEMS microphones typically include a pressure-sensitive diaphragm etched directly on a silicon chip (e.g., MEMS microphones marketed by Akustica, Inc. (Pittsburgh, Pa.) are available with a footprint of 4 mm×4 mm).

Signals acquired from a vibration sensor may be analyzed with respect to energy, duration, amplitude or other characteristics. In various examples, filtering may be used to more easily measure or identify heart sounds. Such filtering may include use of lowpass, highpass or bandpass filters. Vibration information may be used for any of a variety of purposes. For example, a QRS to S1 heart sound may be used to assess electromechanical delays of the heart.

As described herein, an exemplary lead includes a vibration sensor (e.g., accelerometer or other sensor) proximate to one end and a connector at the other end that allows for connection to an implantable device such as the device 100. Such a lead-based sensor is suitable for sensing vibrations of heart sounds.

While a vibration sensor may be included in the case of an implantable pulse generator device, alternatively, a vibration sensor communicates with an implantable device via a lead or through electrical signals conducted by body tissue and/or fluid. In the latter instance, the sensor may be positioned to advantageously sense vibrations associated with cardiac events. For example, an epicardial accelerometer may have improved signal to noise for cardiac events compared to an accelerometer housed in a case of an implanted pulse generator device.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264. Trigger IEGM storage also can be achieved by magnet.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds (e.g., HF indications like pulmonary edema); detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses in a range of joules, for example, conventionally up to about 40 J, as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In low-energy cardioversion, an ICD device typically delivers a cardioversion stimulus (e.g., 0.1 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the ICD device initiates defibrillation therapy.

While an ICD device may reserve defibrillation as a latter tier therapy, it may use defibrillation as a first-tier therapy for VF. In general, an ICD device does not synchronize defibrillation therapy with any given portion of a ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two current pathways.

Figure 3:
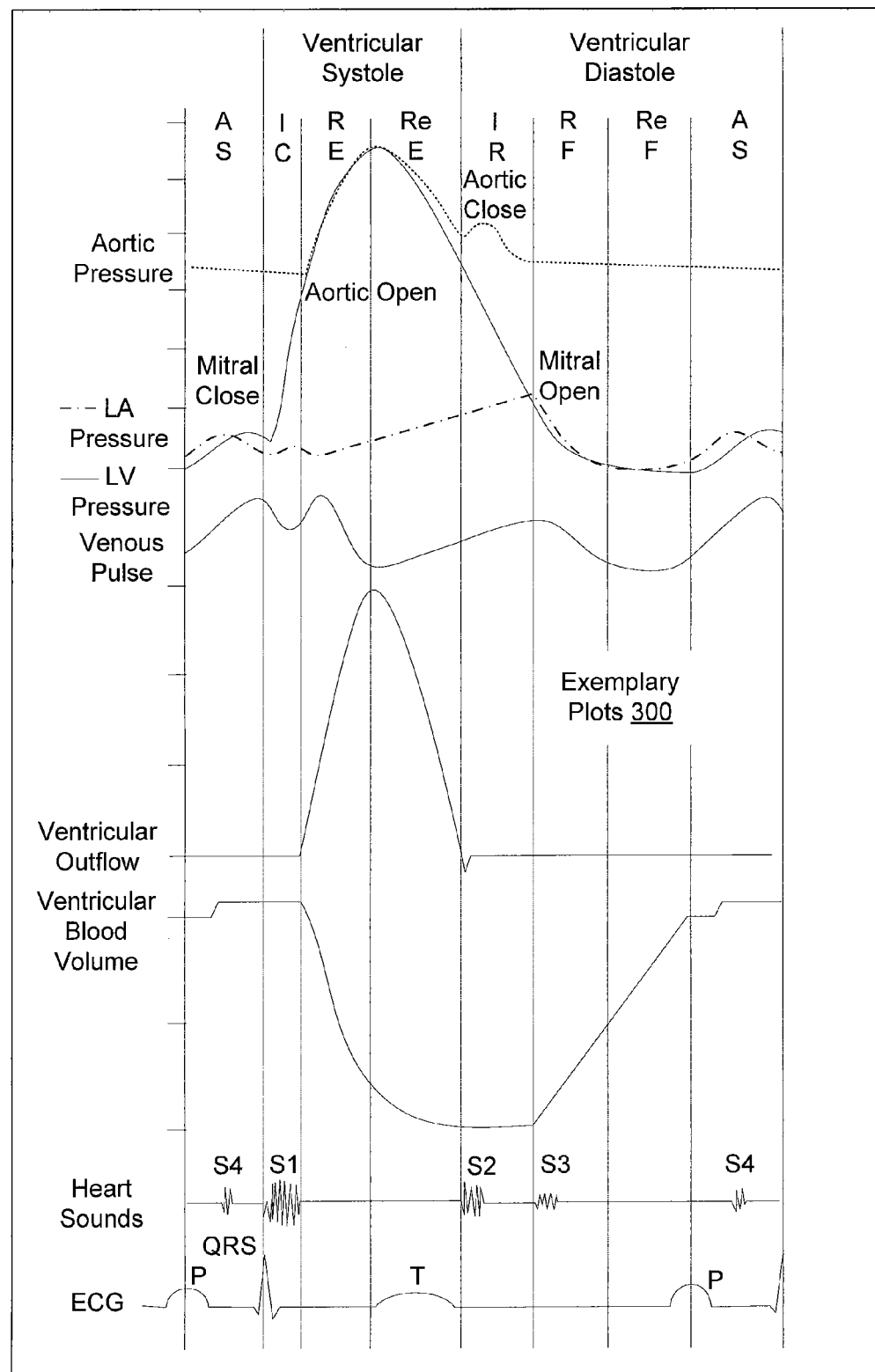
FIG. 3 is a diagram of various parameters and their variations during a cardiac cycle as typical of a Wigger diagram.

FIG. 3 shows a plot 300 of various parameters versus time during a cardiac cycle. The plot 300 is adapted from a Wigger diagram in an article entitled "Cardiovascular System Review" by Rogers and Humburg. The plot 300 shows various phases of the cardiac cycle including atrial systole (AS), isovolumic contraction (IS), rapid ejection (RE), reduced ejection (ReE), isovolumic relaxation (IR), rapid filling (RF), and reduced filling (ReF). In particular, the plot 300 illustrates how various parameters vary during ventricular systole and diastole. The parameters include aortic pressure, left atrial pressure, left ventricular pressure, venous pulse, ventricular outflow, ventricular volume, heart sounds, electrical activity (e.g., electrocardiogram) and valve dynamics. As described herein, various parameters are used to determine heart condition and to optionally adjust therapy.

A condition of particular interest is diastolic heart failure (DHF), which is generally defined to be a heart failure with ejection fraction (EF) greater than 50% (e.g., a "normal" ejection fraction). A relationship between left ventricular ejection fraction (LVEF) and heart failure typically exists where a decrease in LVEF corresponds to a progression or worsening of heart failure. A study by Tanner et al. "The prevalence of anemia in chronic heart failure," *Int J Cardiol.* 2002; 86(1):115-21, found an inverse relationship between NYHA class and LVEF with class I patients having an average ejection fraction of 45%, class II patients having an average LVEF of 32%, class IIII patients having an average LVEF of 25% and class IV patients having an average LVEF of 25%. Consequently, robust diagnosis of DHF should consider parameters other than EF.

Gibson and Francis, "Clinical Assessment of Left Ventricular Diastolic Function," *Heart* 2003; 89:231-238, mention a variety of parameters related to diastolic function. For example, a short isovolumic relaxation time (IVRT) may indicate a raised filling pressure, a poor prognosis and possibly conventional treatment with diuretics and ACE inhibitors and incoordinate relaxation may be a marker of diastolic disease. A normal range of IVRT is typically about 60 ms to about 90 ms.

Referring to the plot 300, isovolumic relaxation (IR) occurs during ventricular diastole and is demarcated approximately by closure of the aortic valve and second heart sound (S2) and approximately by opening of the mitral valve and third heart sound (S3), which is more prominent in children and those with abnormal ventricular function when compared to normal adults. In general, onset of IR is more well-defined in comparison to the end of IR. During IR, ventricular pressure decreases; however, the blood volume remains constant because the valves are closed. The volume of blood that remains in a ventricle is called the end-systolic volume and is typically about 50 ml for the left ventricle. According to the study by Gibson and Francis, onset of isovolumic relaxation time commences with aortic valve closure, which can be identified by the aortic component (A2) of the second heart sound (S2); however, the end is less well defined. Gibson and Francis note that in normal adults, the time interval from A2 to mitral cusp separation is about 60 ms and that to the onset of Doppler flow is approximately 85 ms. As described herein, S2 or A2 may be used to determine cardiac condition, to determine one or more pacing parameters or performance of a cardiac pacing therapy. For example, S2 or A2 may represent events from which time to a subsequent event is measured or S2 or A2 may be analyzed for characteristics that may indicate heart condition or performance of a therapy. In turn, selection or adjustment of a therapy may occur. Gibson and Francis also note that a very short IVRT is a reliable sign of a raised atrial pressure and a prolonged IVRT indicates a combination of ventricular disease with normal or near normal filling pressure. Thus, as described further below, IVRT may act as an indicator of disease.

The third heart sound (S3) has been linked to flow between the left atrium and the left ventricle, more generally LV filling, and thought to be due to cardiohemic vibrations powered by rapid deceleration of transmitral blood flow. However, according to Manson et al., the oscillations may not have high enough amplitude or frequency to be heard as an S3 unless there is sufficiently rapid fluid deceleration (of the Doppler E-wave contour) with sufficient cardiohemic coupling ("Relationship of the Third Heart Sound to Transmitral Flow Velocity Deceleration," *Circulation.* 1995; 92:388-394). S3 typically occurs about 130 ms to about 200 ms after S2.

A variety of mechanisms provide for LV filling, some of which occur during the systolic phase of the cardiac cycle. During ejection, the LV undergoes counterclockwise torsion and clockwise recoil of torsion or untwisting before mitral valve opening, especially during the IVRT. This recoil is associated with release of restoring forces that had been accumulated during systole and is thought to contribute to diastolic suction and hence LV filling. Early diastolic annular motion is a potential marker of LV recoil and, in general, peak annular velocity ($E_m$) should precede peak mitral flow velocity (E). These velocities are explained in more detail with respect to FIG. 5. As conditions like mitral regurgitation (MR) are related to flow, S3 may include components stemming from MR.

A fourth heart sound (S4) may be present in the late stage of diastole and associated with atrial contraction, or kick, where the final 20% of the atrial output is delivered to the ventricles. If the ventricle is stiff and non-compliant, as in ventricular hypertrophy due to long-standing hypertension, the pressure wave generated as the atria contract produces a fairly distinct S4.

Gibson and Francis identify incoordinate relaxation or incoordination as a major cause in prolonging IR as it occurs around the transition from IR and rapid ventricular filling (RF). Incoordinate relaxation refers to changes in shape of the left ventricle during early diastole and may be assessed by comparing longitudinal motion along a major axis of the left ventricle to motion along a minor axis. In general, the major axis of the left ventricle may be defined by the apex of the left ventricle and the atrioventricular ring (AVR) or mitral annulus (MA). Studies have shown that the apex of the left ventricle remains relatively stationary while the mitral annulus has a significant displacement component along the axis. Thus, observation of the mitral annulus may provide useful information, for example, amplitude, velocity and/or timing information.

Various studies indicate that amplitude of the mitral annulus correlates with ejection fraction and that timing of onset of mitral annulus movement may be used in conjunction with a marker (e.g., preferably insensitive to changes in heart rate or loading conditions) to determine cardiac condition.

A study by Rivas-Gotz et al., "Time Interval Between Onset of Mitral Inflow and Onset of Early Diastolic Velocity by Tissue Doppler: A Novel Index of Left Ventricular Relaxation: Experimental Studies and Clinical Application," *J Am Coil Cardiol* 2003; 42(8):1463-1470, proposed an index and a time interval that could be used to diagnose cardiac condition. The time interval is determined by the time of onset of mitral inflow or transmitral flow (from the left atrium to the left ventricle), $T_E$, and the time of onset of early diastolic velocity of the mitral annulus, $T_{Ea}$, wherein $T_{Ea}$ occurs generally after $T_E$ (noting a distinction between $E_a$ and the aforementioned parameter $E_m$).

Figure 4:
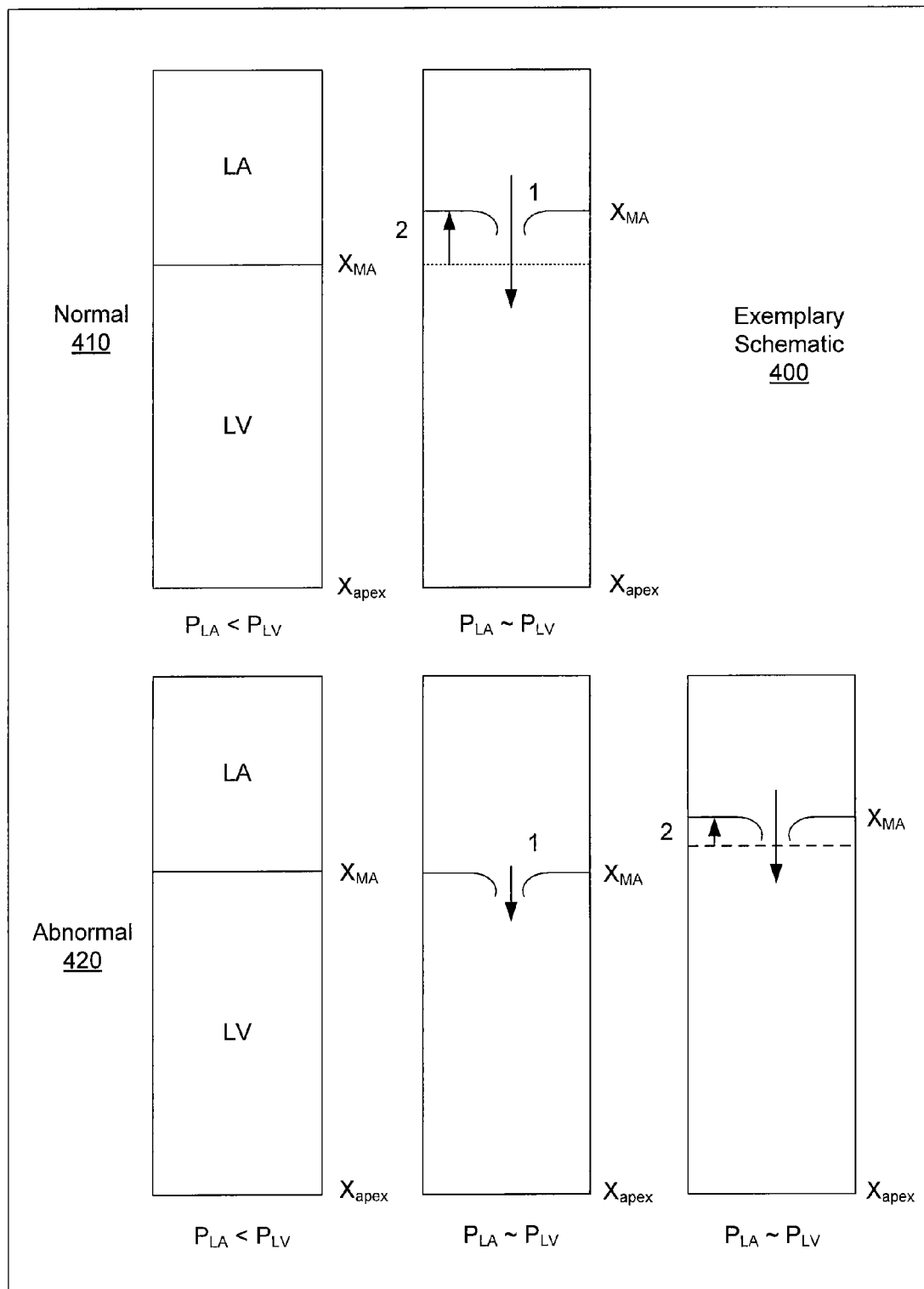
FIG. 4 is an exemplary schematic of normal cardiac condition and abnormal cardiac condition and associated mechanisms.

FIG. 4 shows a schematic 400 representative of normal cardiac condition 410 and abnormal cardiac condition 420. The schematic 400 aids in explanation of mechanisms associated with the times $T_E$ and $T_{Ea}$, focusing on the major axis of the left ventricle. For both cases 410, 420, at a time during late systole or early diastole, the pressure of the left ventricle exceeds the pressure of the left atrium; however, as time progresses, the pressure of the left ventricle falls as the pressure of the left atrium rises. When the pressures are approximately equal, a first mechanism (1) occurs wherein the mitral valve opens which may thereby allow for flow of blood from the left atrium to the left ventricle. For the normal cardiac condition 410, a second mechanism (2) occurs nearly synchronously with the first mechanism (1). The second mechanism (2) involves upward movement (cephalad) of the mitral annulus (MA), i.e., away from the apex of the left ventricle. In the schematic 400, $X_{MA}$ represents a position of the MA along the major axis of the left ventricle and $X_{apex}$ represents a position of the apex of the left ventricle. In the Rivas-Gotz et al. study, the $T_{Ea}$ and $T_E$ times were measured using Doppler flow and Doppler tissue techniques, respectively, with respect to peak R wave time. According to the study by Rivas-Gotz et al., the average time interval $T_{Ea}$-$T_E$ in normal humans is approximately 3 ms; thus, in the schematic 410, the first mechanism (1) occurs about 3 ms prior to the second mechanism (2).

The study by Rivas-Gotz et al. also provides data for humans with impaired ventricular relaxation as an abnormal group and a pseudonormal group. The average time interval for the abnormal group was about 33 ms and the average time interval for the pseudonormal group was about 37 ms. Thus, in these groups with impaired ventricular relaxation, a significant delay existed between $T_{Ea}$ and $T_E$ or onset of the first mechanism (1) and onset of the second mechanism (2). Therefore, the abnormal schematic 420 shows two separate events: onset of the first mechanism (1) and onset of the second mechanism (2). While the second mechanism includes an arrow representing flow, movement of the mitral annulus is generally opposite flow direction and hence flow through the open mitral valve increases in part due to movement of the mitral annulus.

The time intervals given by Rivas-Gotz et al. may be compared to those of Gibson and Francis. For example, Gibson and Francis noted an A2 to mitral opening interval of about 60 ms±20 ms and an A2 to onset of Doppler flow of about 85 ms±15 ms. While these data indicate that the time interval between mitral opening and Doppler flow is about 25 ms, Gibson and Francis also note that mitral cusp separation precedes the onset of flow on pulsed Doppler by about 10 ms to 12 ms in normal individuals and may extend up to 100 ms in patients with disease. Overall, these data indicate that the second mechanism (2) may be responsible for most of the flow from the left atrium to the left ventricle in early ventricular diastole. An exemplary method may determine that a cardiac condition exists if the time between mitral valve opening and onset of flow (or indicator thereof or ventricular motion related to flow) exceeds approximately 25 ms. In another exemplary method, a long-term average of such a difference may be used and compared to a short-term average using one or more criteria to determine if a cardiac condition exists, is improving or is worsening. An exemplary method may use such information to select or adjust one or more parameters for cardiac pacing.

The Gibson and Francis study also discusses peak inward motion of the atrioventricular ring (AVR) and includes M mode echocardiographs that show, for normal individuals, peak inward motion approximately synchronous with heart sound A2. The study notes that the synchronous pattern of AVR motion is lost with left bundle branch block (e.g., peak inward motion occurring approximately 100 ms after A2). S2 or A2 or other indicator of aortic valve state may be used by an exemplary method, for example, in comparison to onset of flow (or indicator thereof or ventricular motion related to flow). In one example, a time difference between S2 or A2 and onset of flow (or indicator thereof or ventricular motion related to flow) in excess of approximately 100 ms may indicate a cardiac condition. In another exemplary method, a long-term average of such a difference may be used and compared to a short-term average using one or more criteria to determine if a cardiac condition exists, is improving or is worsening. An exemplary method may use such information to select or adjust one or more parameters for cardiac pacing.

Various exemplary methods, devices, systems, etc., disclosed herein rely on direct and/or indirect measurements that indicate substantially asynchronous occurrence of mitral valve opening and upward movement of the mitral annulus. Various exemplary methods, devices, systems, etc., disclosed herein optionally rely on direct and/or indirect measurement of onset of upward movement of the mitral annulus with reference to one or more other events. As described in more detail below, various exemplary methods, devices, systems, etc., disclosed herein rely on sensing cardiohemic vibrations to determine cardiac condition, to select or adjust cardiac pacing therapy, or to determine performance of a cardiac pacing therapy.

Figure 5:
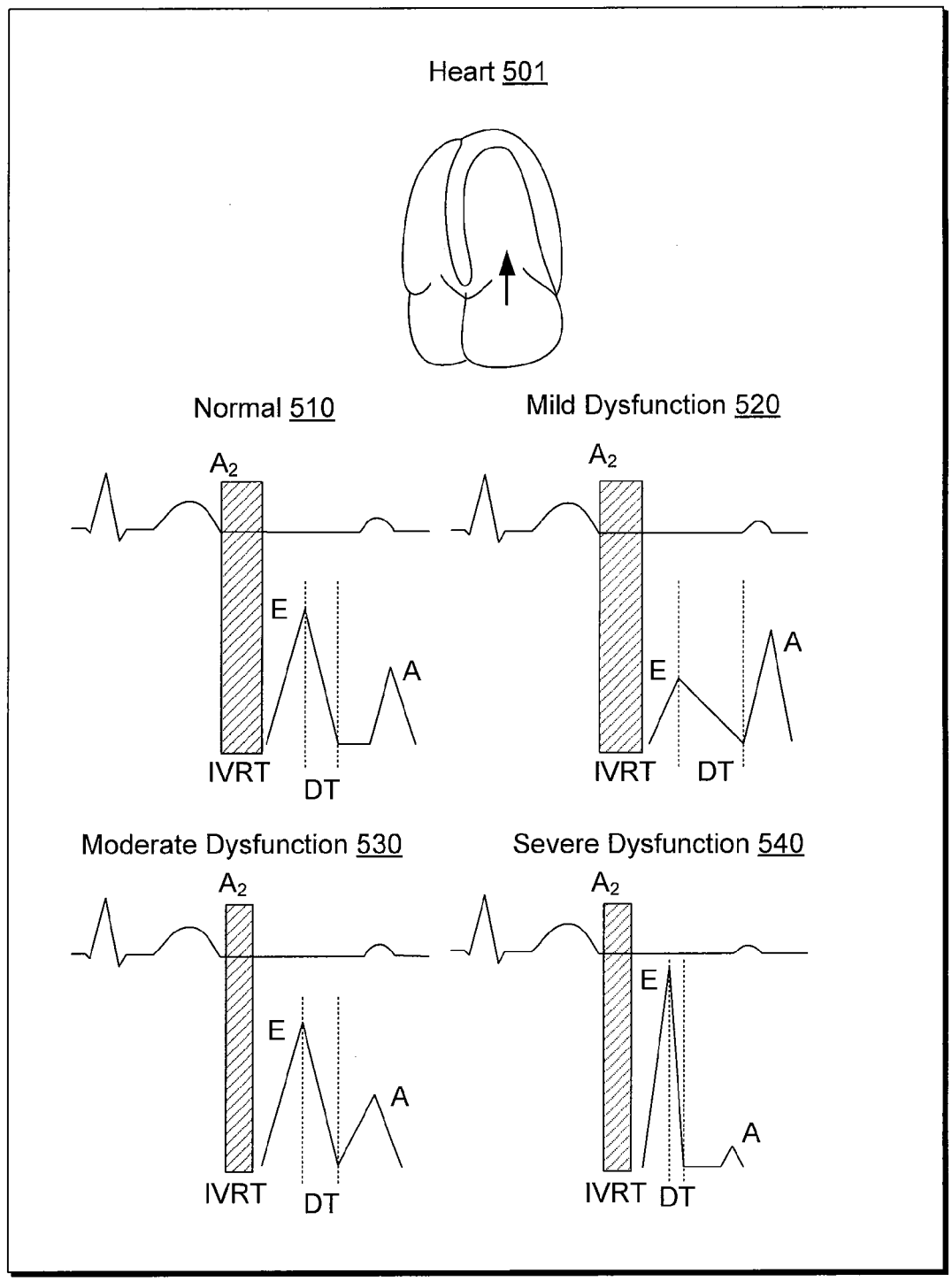
FIG. 5 is a diagram of echocardiography data for normal and abnormal cardiac conditions.

FIG. 5 shows a heart 501 and direction of blood flow from the left atrium, through the mitral valve, during filing of the left ventricle. Simplified schematic plots of typical ECG and echocardiography data are shown for normal 510, mild dysfunction 520, moderate dysfunction 530 and severe dysfunction 540. As already discussed, IVRT may be determined from the A2 sound (e.g., via phonocardiography or other technique) to the onset of the E wave (e.g., tissue Doppler imaging of onset of blood flow from the left atrium to the left ventricle). The time interval DT is the deceleration time of blood flow from the left atrium to the left ventricle. An A wave represents flow from the left atrium to the left ventricle caused by atrial contraction.

Gibson and Francis note age related changes in cardiac function. In particular, aging prolongs IVRT, reduces peak E wave velocity and E/A ratio, increases E wave deceleration time (DT) and decreases the peak velocity of early diastolic AV ring retraction. Gibson and Francis also note effects or evidence of a raised left atrial pressure: shortening of IVRT, increase in peak E wave velocity and E/A ratio, decrease in E wave deceleration time (DT), increase in diastolic pulmonary venous velocity and an increase in the ratio of E to peak velocity of early diastolic AV ring retraction. With respect to the plots of FIG. 5, aging may be understood by comparing normal 510 to mild dysfunction 520 whereas an increase in left atrial pressure may be understood in comparing mild dysfunction 520 to moderate 530 and severe dysfunction 540. Consequently, the plots of FIG. 5 represent two processes or phases, which are referred to herein as normal aging and disease phases.

Figure 6:
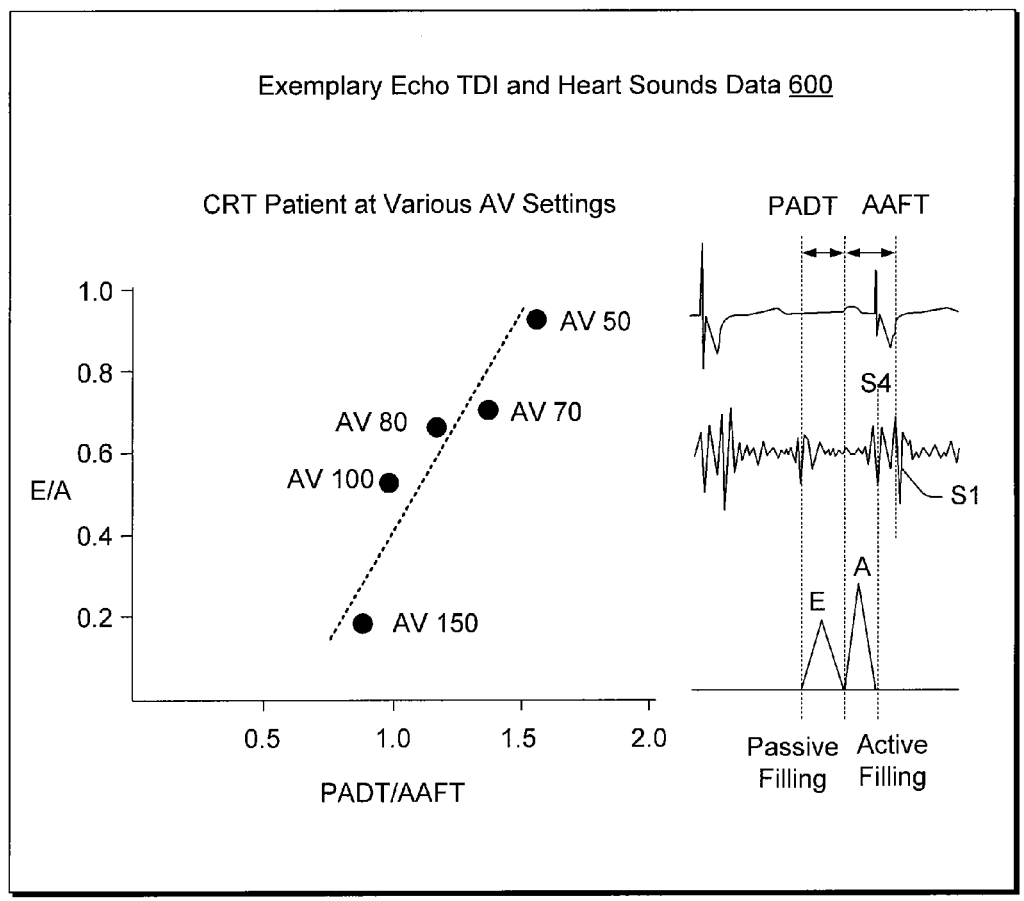
FIG. 6 is a series of plots for echocardiograph and heart sound data for a patient treated with cardiac resynchronization therapy (CRT).

FIG. 6 shows exemplary echocardiograph tissue Doppler ultrasound and heart sound data for a CRT patient 600. For this patient, the E/A ratio is plotted versus the ratio of the pre-atrial diastolic time (PADT) and the atrial activation filling time (AAFT). The E/A ratio increases with decreasing AV delay and as AV delay decreases, the PADT/AAFT ratio increases, which is a ratio of passive filling time to active filling time. As indicated by the heart sound signal, S4 occurs during AAFT at the end of the echocardiograph A wave while passive filling, as approximated by the E wave, commences around S2 and S3.

Figure 7:
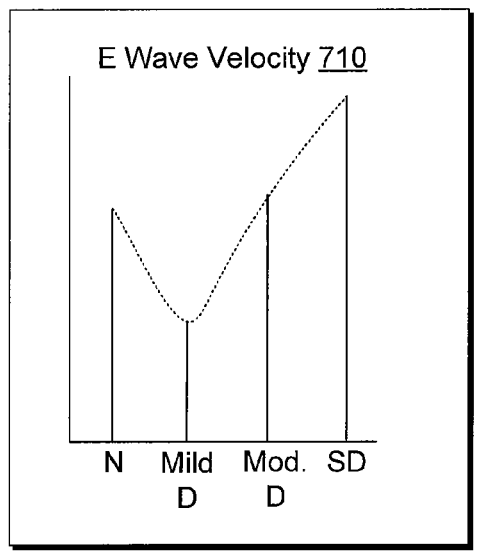
FIG. 7 is a series of plots exhibiting trends associated with changes in cardiac condition.
Figure 7:
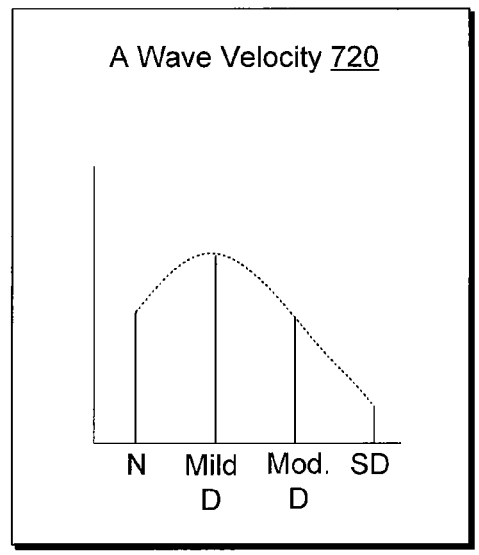
Figure 7:
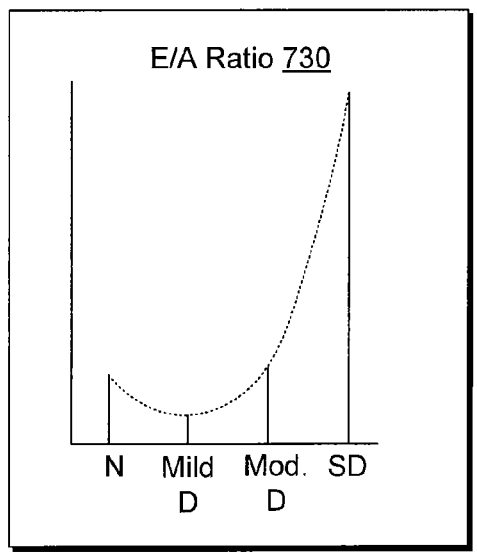
Figure 7:
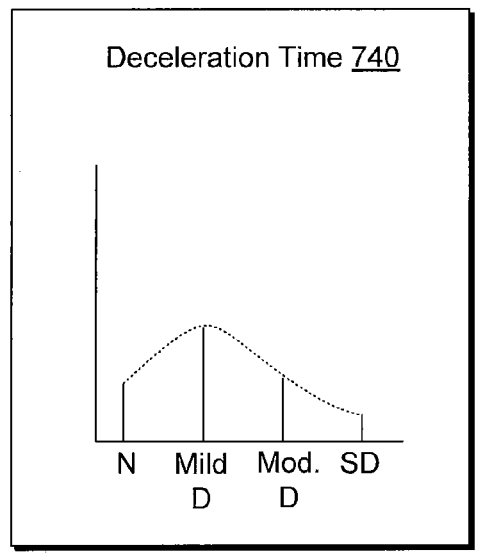
Figure 7:
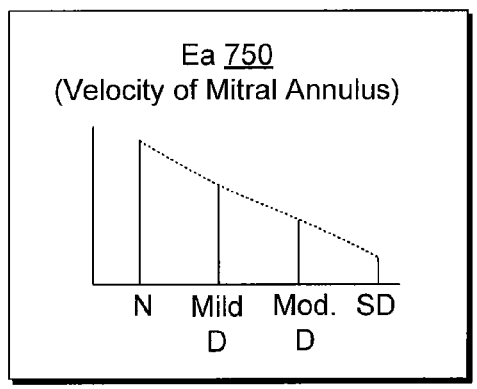
Figure 7:
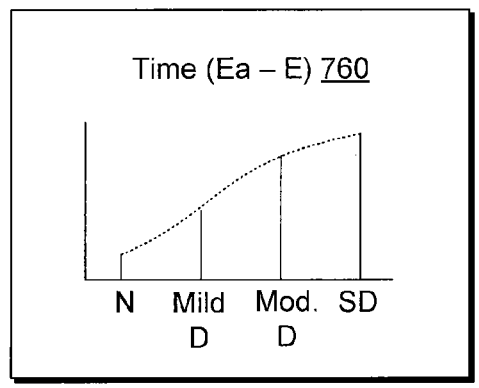

FIG. 7 shows a series of plots 700 for various parameters along with suggested trends. A plot of peak E wave velocity versus condition 710 indicates that during the disease phase "Mild to Severe", E wave velocity increases. A plot of A wave velocity versus condition 720 indicates that during the disease phase "Mild to Severe", A wave velocity decreases. A plot of E/A ratio versus condition 730 indicates that during the disease phase "Mild to Severe", E/A ratio increases. A plot of deceleration time versus condition 740 indicates that during the disease phase "Mild to Severe", deceleration time decreases. A plot of Ea versus condition 750 indicates that during aging (e.g., "Normal to Mild") and diseases phases ("Mild to Severe"), Ea decreases. A plot of $T_{Ea-E}$ versus condition indicates that during aging (e.g., "Normal to Mild") and disease phases ("Mild to Severe"), $T_{Ea-E}$ increases.

With respect to E and A waves, Gibson and Francis note that E/A (plot 730) falls with age (e.g., "Normal to Mild") such that for the elderly, atrial filling is normally dominant at rest. However, as heart rate increases and diastolic period shortens, the A wave becomes superimposed on the declining E wave, which can increase its apparent amplitude. So-called "summation filling" may occur at very fast heart rates where diastolic is reduced by abnormal prolongation of systole. Summation filling is reflected by a high degree of superimposition of E and A waves. Where AV interval and heart rate are not appropriately timed, such superimposition can occur as well. Some have called an optimal AV delay, the shortest AV delay that does not truncate the A wave (see, e.g., FIG. 6).

As already mentioned, the third heart sound (S3) is thought to be associated with cardiohemic vibrations. Spring models also exist in which the spring constant "k" is represented by the thickness of the left ventricle and mass "m" by blood in the left ventricle. Given such a model, the ratio of k/m can help determine acoustic quality of the third heart sound (S3), which can yield information on the dysfunction of the left ventricle in ischemic heart disease.

Another approach recognizes that kinetic energy may be converted to vibrational energy or sound energy. Kinetic energy is proportional to mass and to velocity squared. With respect to velocity of blood flow between the left atrium and the left ventricle, velocity can increase as cross-sectional flow area of the mitral valve decreases (e.g., average velocity is approximately equal to flow rate divided by cross-sectional flow area). Thus, blood KE can be related to state of the mitral valve.

Figure 8:
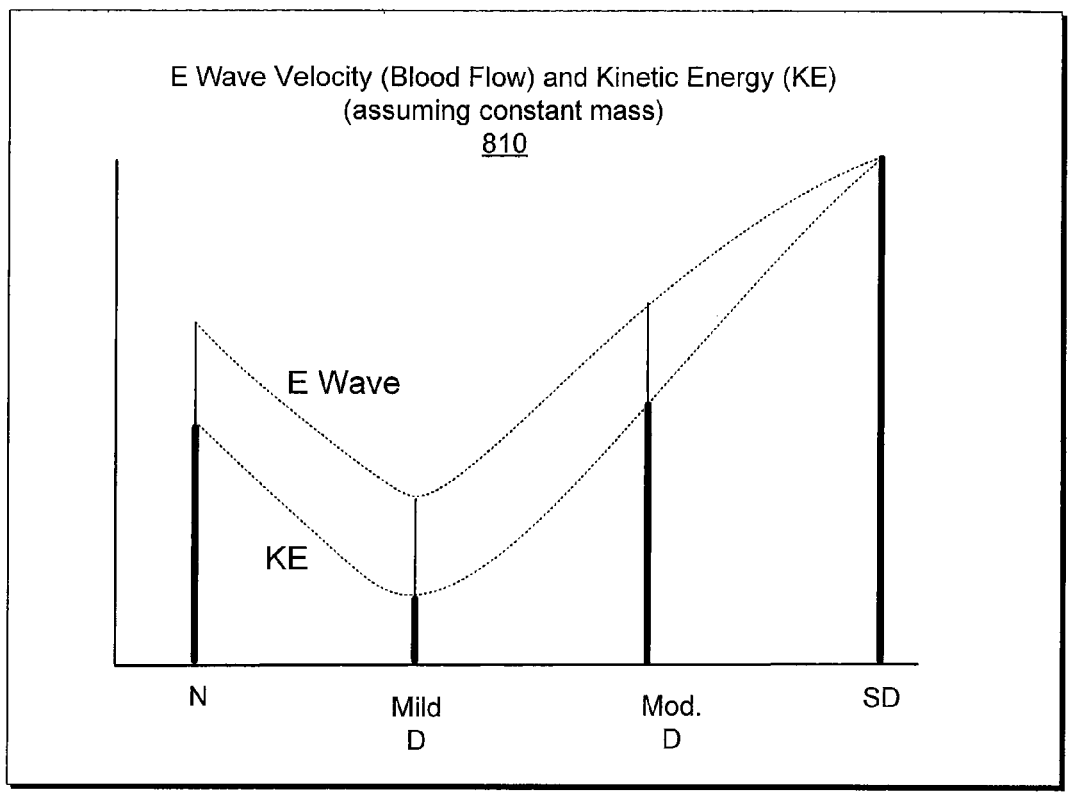
FIG. 8 is a plot of E wave and kinetic energy versus cardiac condition and a plot of deceleration time of blood associated with left ventricular filing versus cardiac condition.
Figure 8:
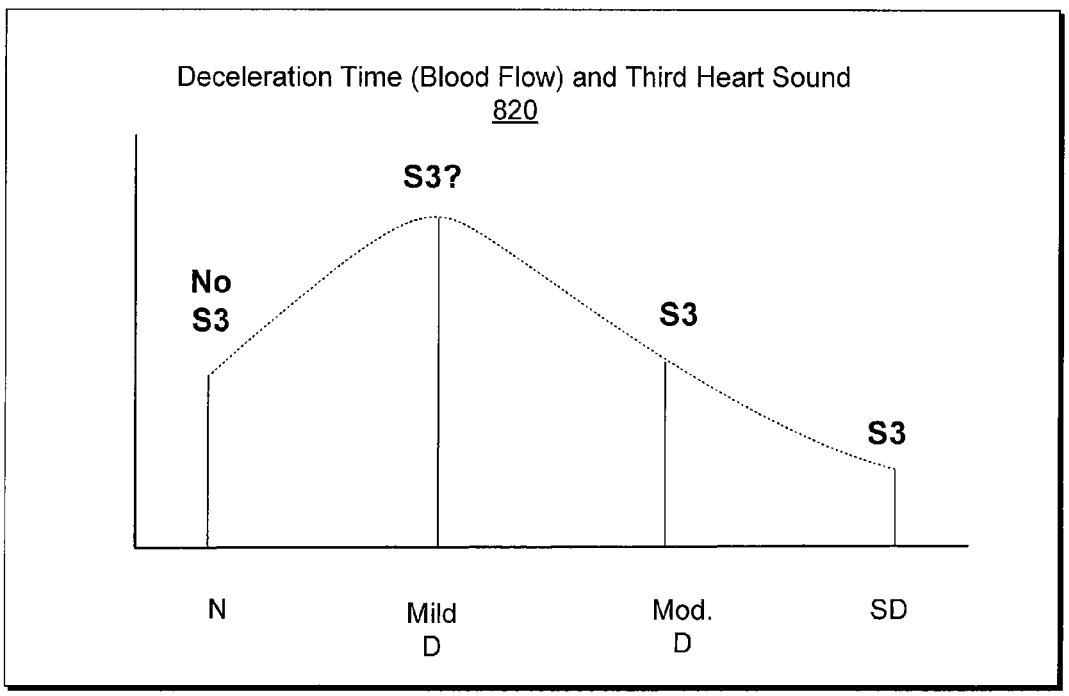

FIG. 8 shows a plot 810 of E wave velocity and kinetic energy (KE) versus condition and a plot 820 of deceleration time (DT) versus condition, noting presence of S3. As mentioned, S3 tends to "disappear" in an aging adult and tends to reappear with cardiac disease. For example, the S3 heart sound is present in only about 5% of adults over the age of 40 (see the range of "Normal to Mild Dysfunction" in the plots 810 and 820) and tends to increase in those over the age of 70. With respect to S4, presence of S4 increases with age. Various exemplary techniques optionally rely on S3 information and S4 information, recognizing that the population having both the S3 and the S4 heart sounds, after the age of 40, is typically less than the population with the S3 heart sound.

Referring to the aforementioned aging and disease phases, the plot 810 indicates (for an assumed constant mass) that kinetic energy decreases with age ("Normal to Mild") but increases with disease ("Mild to Severe"). The plot 820 reflects already reported data that suggests a relationship between S3 and deceleration time. In particular, force transmitted to the ventricle and the blood pool and surrounding structures by the deceleration of transmitral flow generates oscillations where, the greater the deceleration, the greater the force that is applied during the period of deceleration and the higher the amplitude and frequency of the resulting oscillation.

Alone or together, the plots 810 and 820 suggest an increase in cardiohemic vibrations during progression of disease ("Mild to Severe"). Further, with respect to deceleration, force is proportional to acceleration (F=ma). Hence, increases in deceleration and velocity can result in increased kinetic energy and force, which, in turn, can dissipate as vibration or sound energy.

While various techniques described herein refer to presence or absence of S3, there will always be vibration associated with left ventricular filling. As described herein, an exemplary intrathoracic vibration sensor can sense vibration associated with left ventricular filling. Sensed vibration information may be used for any of a variety of purposes. Any determination as to presence or absence of S3 may be made with respect to one or more criteria. For example, where vibration is insufficient to result in an audible signal to a clinician, then that vibration may be associated with absence of S3. However, as already mentioned, some vibration exists, which may be sensed using an intrathoracic vibration sensor (see, e.g., the sensor 1060 of FIG. 10).

Figure 9:
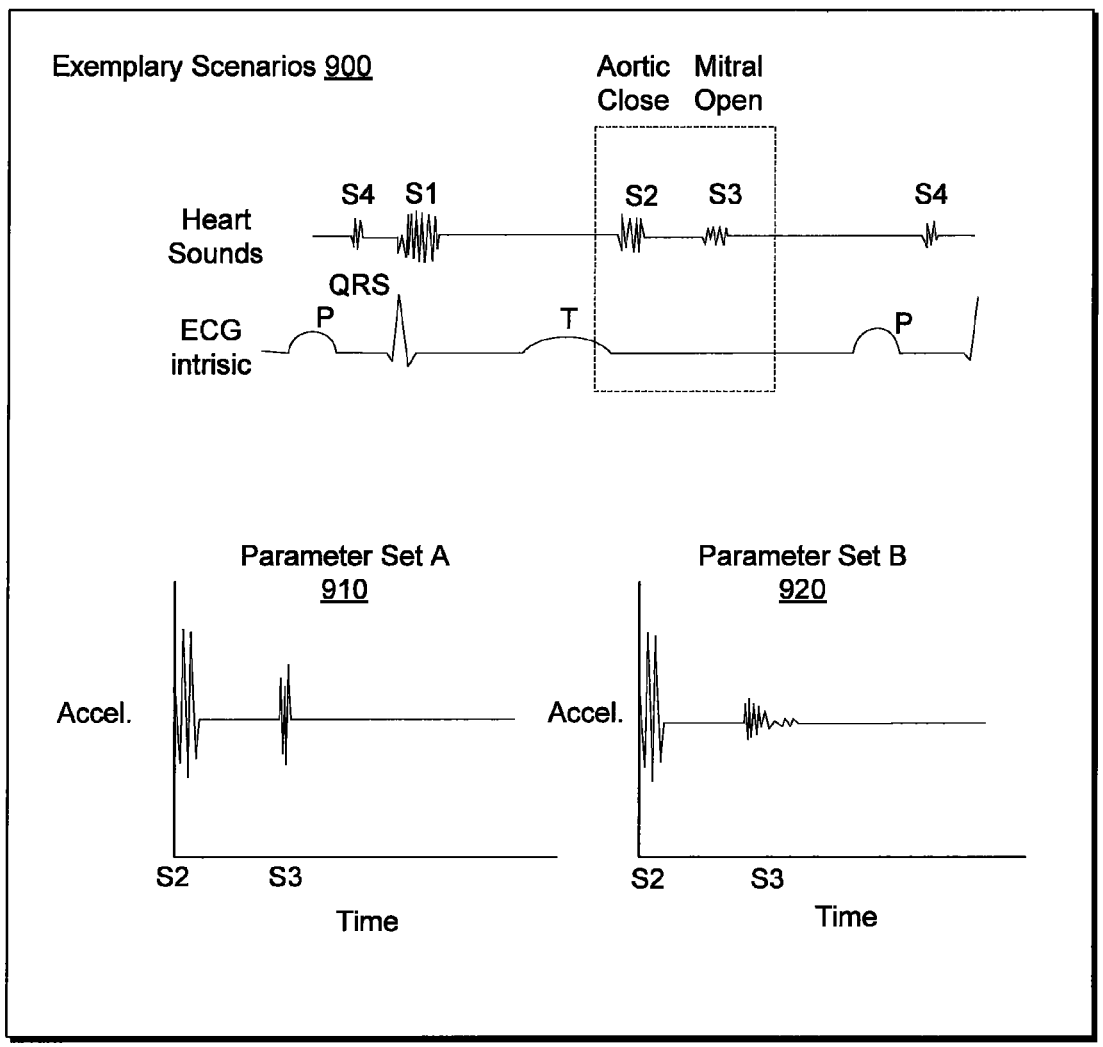
FIG. 9 is a diagram of exemplary scenarios associated with heart sounds versus time.

FIG. 9 shows exemplary scenarios 900 with respect to the third heart sound (S3). While an ECG for intrinsic activity is shown with vibrations overtime, the plots 910 and 920 pertain to cardiac pacing. Vibrations may be sensed using acceleration or phonocardiography or other suitable techniques. For a first parameter set (parameter set A), a plot of vibration versus time 910 exhibits a distinct S3 whereas, for a second parameter set (parameter set B), a plot of vibration versus time 920 exhibits a less distinct S3. Such information may be used in conjunction with an algorithm to optimizing one or more pacing parameters.

The exemplary scenarios 900 illustrate use of information associated with heart sounds to determine how one or more cardiac pacing parameters perform. The exemplary scenarios 900 may also allow for determination degree of diastolic heart failure. The exemplary scenarios 900 optionally rely on other information.

An exemplary method may rely on sound, or more generally vibration, (e.g., through use of a vibration sensor) to determine characteristics of heart sounds, such as, but not limited to, dispersion of the third heart sound (S3) (e.g., duration, etc.).

An exemplary method includes sensing information after closure of the aortic valve and prior to an atrial contraction of the subsequent cardiac cycle, the information representative of the state of the mitral valve and, based at least in part on the information, deciding whether a diastolic abnormality exists. Such an exemplary method optionally includes sensing left atrial pressure and/or sensing vibration. Such sensing may sense the third heart sound.

Various exemplary methods, devices, systems, etc., optionally account for respiration. For example, respiratory sinus arrhythmia involves slowing of the sinus heart rate during an exhalation phase and a quickening of sinus heart rate during an inhalation phase. Accordingly, data acquisition during late ventricular systole and/or early ventricular diastole may occur based on respiratory phase. Such a data acquisition technique may act to reduce noise and provide a better determination of cardiac condition, therapy performance or therapy optimization.

Figure 10:
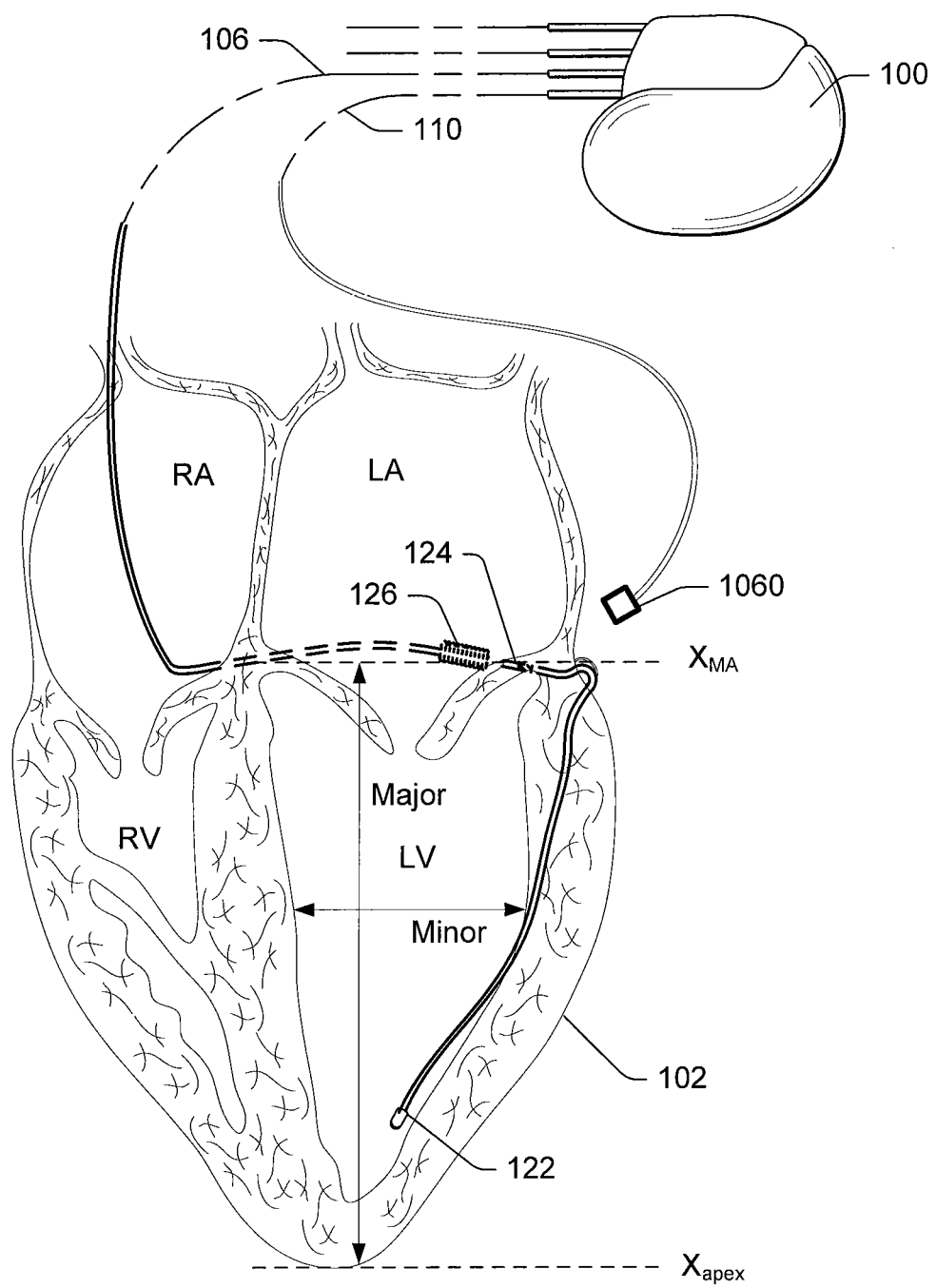
FIG. 10 is a diagram of an exemplary pacing device that includes a lead-based vibration sensor for sensing cardiohemic vibrations.

FIG. 10 shows an exemplary device 100 with a lead 106 as described with reference to FIGS. 1 and 2. The lead 106 includes one or more electrodes 122, 124, 126 positioned proximate to the left ventricle (LV) of the heart 102. In this example, the lead 106 passes from the right atrium (RA) through the ostium into the coronary sinus and into a tributary thereof. The electrodes 124, 126 are positioned on in the coronary sinus while the electrode 122 is positioned proximate to the apex of the left ventricle. The exemplary device 100 includes a case or other electrode proximate to the device 100. Accordingly, the exemplary device 100 is capable of measuring motion of the heart and in particular capable of direct and/or indirect measurement of upward (cephalad) motion of the mitral valve (e.g., mitral annulus or atrioventricular ring). In this example, upward motion corresponds to motion predominantly along the major axis of the left ventricle. The exemplary device 100 optionally measures onset of such upward motion during early diastole and optionally compares an onset time to one or more other event times. The exemplary device 100 optionally relies on such measurements to determine cardiac condition.

For example, the exemplary device 100 may sense an electrical signal indicative of the position of the electrode 124 and/or 126 with respect to the electrode 122, a case electrode and/or other electrode. In particular, the electrodes 124, 126 in the coronary sinus do not depend heavily on changes in blood volume with respect to a current path to the exemplary device 100. Thus, a shortening of distance between such electrodes and the exemplary device 100 may correspond to upward motion of the mitral annulus during early ventricular diastole.

Various exemplary methods, devices, systems, etc., described herein optionally rely on direct and/or indirect distance and/or position measurements of the mitral annulus during early ventricular diastole. Impedance measurements may include vibration information associated with left ventricular filling.

FIG. 10 also shows the exemplary device 100 with a lead 110 as described with reference to FIGS. 1 and 2. In this example, the lead 110 includes an intrathoracic vibration sensor 1060. The sensor 1060 may be positioned proximate to the heart, on the heart or in the heart. In particular, the sensor 1060 may be positioned proximate to the mitral valve. The device 100 may use the sensor 1060 to determine condition, select a therapy, adjust a therapy, assess performance of a therapy, etc. The device 100 may rely on a combination of measures, for example, impedance and accelerometer measures.

The device 100 may optionally include more than one vibration sensor. In such a configuration, information acquired from one sensor may be used to improve a signal from another sensor. For example, other body vibrations may obscure vibrations associated with left ventricular filling. Where an additional sensor is used, a vibration signal from that sensor may be used to filter a signal from the sensor best suited to sense vibrations associated with left ventricular filling. This arrangement can provide for more robust detection of vibrations associated with left ventricular filling. In another example, one sensor is positioned to sense vibration associated with closure of the aortic valve (e.g., S2 or A2 component of S2). In turn, detection of aortic closure may initiate a sensing window for sensing vibration associated with left ventricular filling and more particularly to the heart sound S3. An accelerometer may also be used to sense acceleration, for example, of the heart along its major axis.

With respect to sensing locations, the sensor 1060 may be placed close to apex and may be an interpericardial sensor. The sensor 1060 may have a patch configuration. An exemplary technique optionally relies on differential techniques, for example, where information acquired from two or more sensors is analyzed to assess heart sounds. Techniques may filter noise such as skeletal noise or other noise, which can interfere with detection of heart sounds. An exemplary technique may filter vibration to focus on vibrations in the range of about 20 Hz to about 100 Hz.

Figure 11:
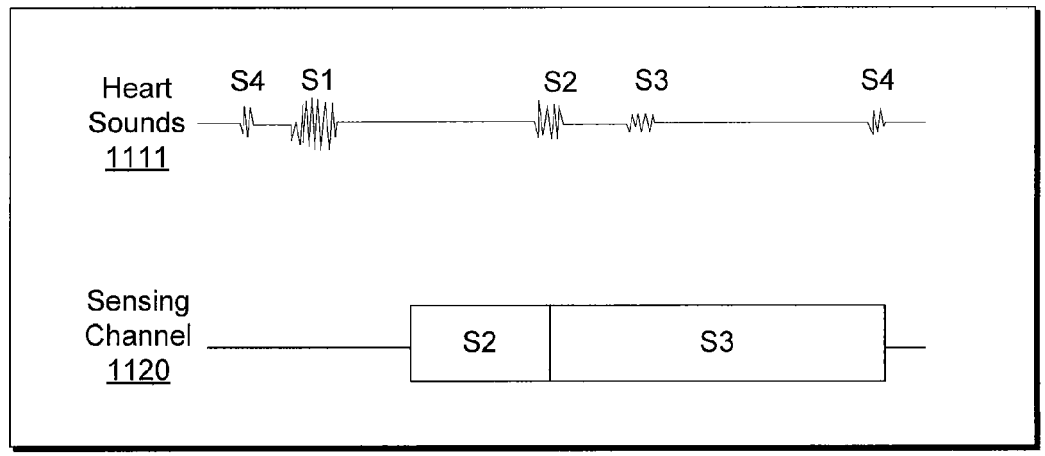
FIG. 11 is an exemplary scheme for sensing cardiohemic vibrations associated with left ventricular filling.
Figure 11:
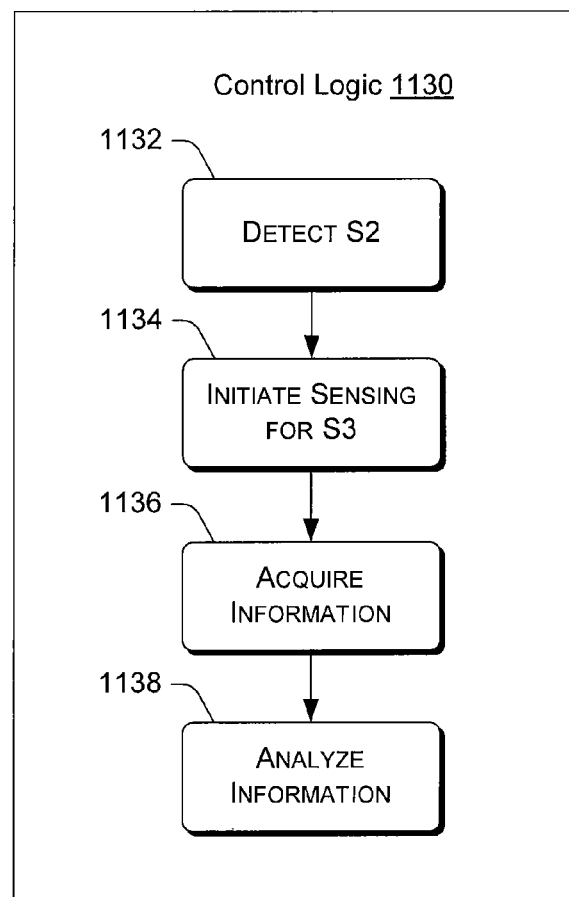

FIG. 11 shows an exemplary scheme 1100 where detection of S2 initiates sensing for S3. A plot 1110 exhibits heart sounds S1, S2, S3 and S4 over a cardiac cycle. A sensing channel 1120 initiates a sensing window S2 upon occurrence a ventricular stimulus, within a certain amount of time following a ventricular stimulus or according to an evoked response sensed via electrical activity. Upon detection of S2, the sensing channel 1120 initiates another sensing window for detection of S3. The sensing parameters used for S3 sensing may be different than those used for S2 sensing as S3 typically has some different characteristics. For example, gain may be adjusted as well as any filtering to filter noise and retain components characteristic of S3. The S3 sensing window may terminate upon sensing S4, upon detection of an atrial event, etc.

Where S2 sensing is not available or not sufficiently robust, then other information may be used to initiate a S3 sensing window. For example, where an electrocardiogram is available, end of a T wave may be used to initiate a S2 window with a subsequent S3 sensing window. If pressure information is available, then a change in slope of left ventricular pressure may initiate a S3 sensing window. If venous pulse pressure is available, then a S3 sensing window may be initiated with respect to a V wave. A S3 sensing window may be adjusted or updated based on trends or changes in one or more parameters. For example, if a pacing device calls for an increased heart rate, then timings associated with S3 sensing may be adjusted accordingly. As already mentioned, an increase in heart rate can alter morphology of E and A waves and thus may alter features of S3.

FIG. 11 also shows control logic 1130 where a detection block 1132 detects S2, an initiation block 1134 initiates sensing for S3, an acquisition block 1036 acquires information relevant to S3 or the time frame S3 may be expected to occur, and an analysis block 1138 that analyzes the acquired information. The control logic 1130 may be implemented in conjunction with the device 100 (see, e.g., the vibrations module 239). The control logic 1130 may be adjusted based on adjustments to therapy or may cause an adjustment to therapy and, in turn, optionally adjust one or more vibration sensing parameters. For example, if the control logic 1130 calls for adjustment to an AV delay or VV delay, then the control logic 1130 may adjust one or more vibration sensing parameters to account for the new AV delay or VV delay.

With respect to the analysis block 1138 an analysis may include comparing one or more features of S3 to a limit or limits. Such a comparison may occur for a particular frequency, frequencies or range of frequencies. For example, the comparison may compare a 25 Hz frequency component peak amplitude to a limit and a 50 Hz frequency component peak amplitude to a limit. Based on such a comparison, the control logic may then decide if one or more pacing therapy parameters need adjustment. The analysis block 1138 may analyze the acquired information using derivatives, integrals, durations, etc.

An exemplary method includes detecting the S2 heart sound; in response to the detecting, initiating sensing for the S3 heart sound; via the sensing, acquiring information for the S3 heart sound; and, based at least in part on the acquired information, adjusting an AV delay or a VV delay of an implantable cardiac resynchronization therapy (CRT) device.

Control logic can calculate a total energy for S3 where an increase in total energy corresponds to an increase in ventricular stiffness. Given a certain degree of stiffness, approaches that rely on adjusting AV to optimize hemodynamics may have less effect. Total energy may be determined using an integral approach where both positive and negative deviations about a baseline are summed. Duration of S3 vibration may be used as an indicator of ventricular health. As described herein, S3 information may be used to determine an AV and/or a VV delay and/or to monitor progression of cardiac disease (e.g., heart failure).

While the device 100 of FIG. 10 and the control logic 1130 of FIG. 11 contemplate use of a sensor to sense vibrations associated with the S3 heart sound, an exemplary device and/or method can other techniques. For example, a pressure sensor may sense pressure associated with the S3 heart sound. Various exemplary techniques may include determining cardiac output (CO) based, at least in part, on one or more pulse pressures.

An exemplary method includes issuing an alert based in part on a sensed heart sound (e.g., vibration measurement). For example, the device 100 of FIG. 10 may sense vibration that indicates a change in the third heart sound (S3). In turn, the device 100 may issue an alert where the alert indicates that AV/PV and VV delays may be inappropriate. Such an alert can be particularly useful where the device 100 cannot reliably optimize these delays without additional information (e.g., echo or TDI information) from a clinician.

Various techniques exist to optimize pacing parameters (e.g., AV, PV, VV, etc.). Such techniques may rely on one or more interventricular conduction delays (IVCDs), which may be in a direction from the right ventricle to the left ventricle (IVCD_RL) and/or in a direction from the left ventricle to the right ventricle (IVCD_LR). In general, a stimulus is delivered to one ventricle and a conducted wavefront is sensed in the other ventricle. Such an IVCD may be referred to as a paced IVCD. Alternatively, a sensed IVCD may be used where an intrinsic event is sensed in one ventricle and a conducted wavefront associated with the sensed intrinsic event is sensed in the other ventricle. In either instance, the IVCD provides information about directional conduction between the ventricles. Such information, as explained below, can be used to optimize one or more cardiac therapy parameters.

For bi-ventricular pacing, a VV delay, the conduction delay time to RV and LV leads (Δ) and interventricular conduction delay (IVCD) are measured. The following equations can apply:

$$\Delta = AR_{LV} - AR_{RV} \text{ or} = R_{LV} - R_{RV};$$

$$\Delta_{PIVCD} = PIVCD\_LR - PIVCD\_RL; \text{ and}$$

IEGM VV=$0.5*(\Delta + \Delta_{PIVCD})$; where a positive sign is for LV pace first and negative sign is RV pace first.

Figure 12:
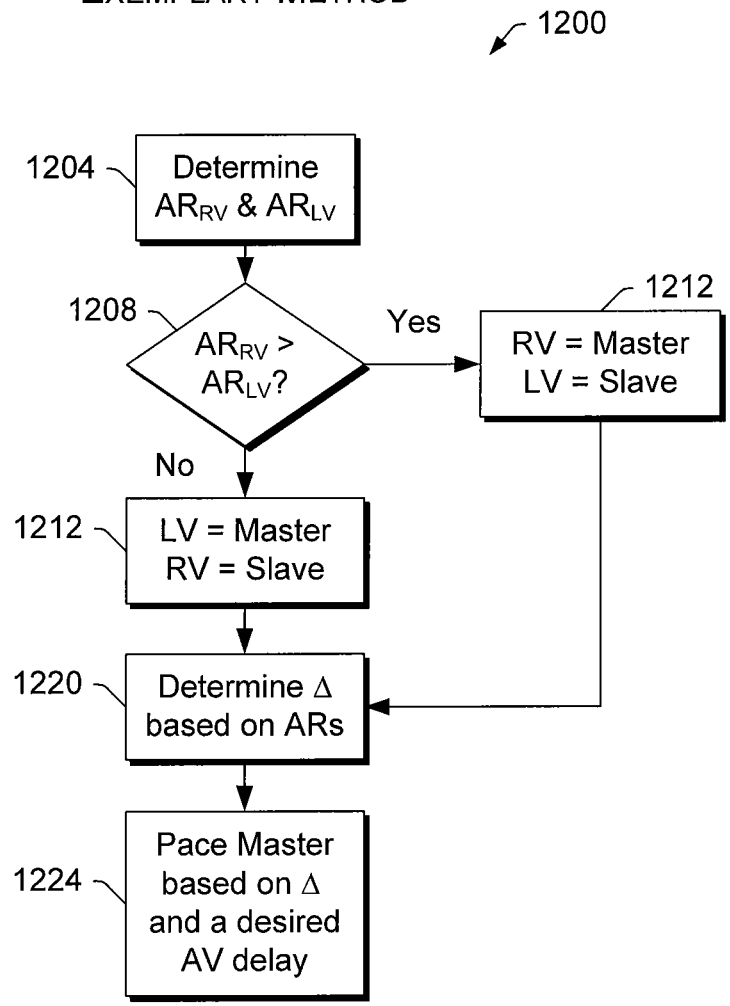
FIG. 12 is a block diagram of an exemplary method for bi-ventricular pacing.

FIG. 12 shows a block diagram of an exemplary method 1200 for ventricular pacing. In a determination block 1204, an implantable device determines an $AR_{RV}$ time and an $AR_{LV}$ time or equivalent times wherein one or both rely on detection of an intrinsic atrial event. A decision block 1208 follows wherein a decision is made as to whether $AR_{RV}$ is greater than $AR_{LV}$. If $AR_{RV}$ exceeds $AR_{LV}$, then in a set block 1212, the right ventricle is set to the master and the left ventricle is set to the slave. If $AR_{LV}$ exceeds $AR_{RV}$, then in a set block 1216, the left ventricle is set to the master and the right ventricle is set to the slave. Both set blocks 1212, 1216 continue in a determination block 1220 which determines a Δ value based on the $AR_{RV}$ and $AR_{LV}$ times. A pace master block 1224 follows wherein the master ventricle is paced based on the A and a desired AV delay. The desired AV delay may be determined, for example, based on an echocardiogram or other study. The AV delay is optionally determined by an implantable device based on sensed information.

Thus, as described with respect to FIG. 12, such an exemplary method includes determining an atrial to ventricular activation time for a right ventricle; determining an atrial to ventricular activation time for a left ventricle; and determining a pacing sequence that paces the right ventricle prior to activation of the left ventricle if the time for the right ventricle exceeds the time for the left ventricle or that paces the left ventricle prior to activation of the right ventricle if the time for the left ventricle exceeds the time for the right ventricle wherein pacing of the prior activated ventricle occurs based at least in part on a difference between the time for the right ventricle and the time for the left ventricle and a desired atrio-ventricular delay. In some instances, an inter-ventricular delay may be used instead of, or in addition, to one or more atrial to ventricular activation times.

Figure 13:
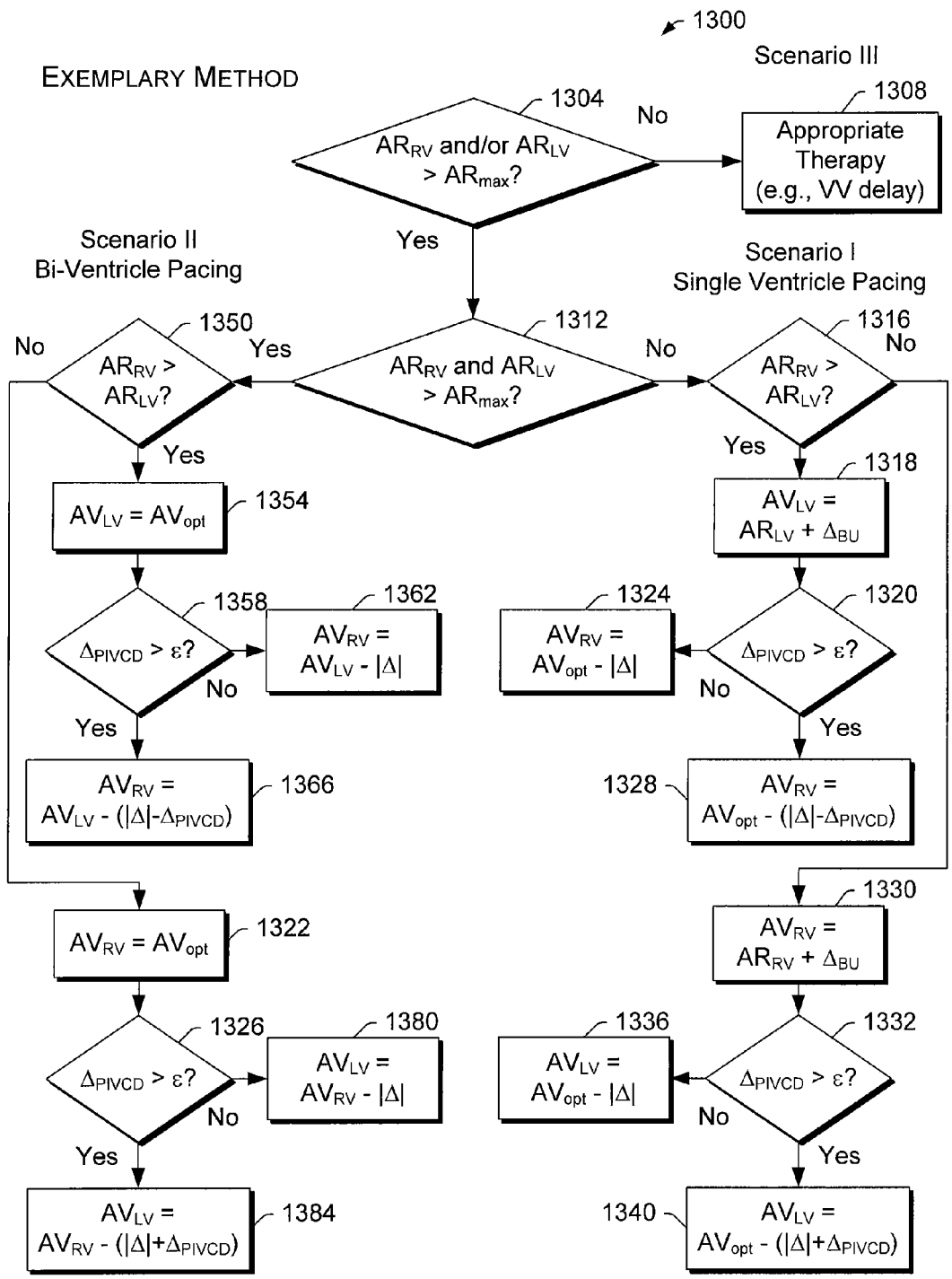
FIG. 13 is a block diagram of an exemplary method for three scenarios for ventricular pacing.

FIG. 13 shows a block diagram of an exemplary method 1300. While the method 1300 pertains to atrial pacing, such a method may omit atrial pacing (e.g., rely on an intrinsic atrial activity, etc.) and/or include atrial pacing and intrinsic atrial activity, etc. (e.g., PR, AR, AV, and/or PV). The exemplary method 1300 includes Scenarios I, II and III as presented above. For example, in a decision block 1304 a decision is made as to whether $AR_{RV}$ and/or $AR_{LV}$ have exceeded a predetermined $AR_{max}$ value. If neither value exceeds $AR_{max}$, then Scenario III follows in no ventricular pacing or other appropriate therapy block 1308. Other appropriate therapy optionally includes therapy that achieves a desirable VV delay. If however one or both values exceed $AR_{max}$, then the method 1300 continues in another decision block 1312. The decision block 1312 decides whether $AR_{RV}$ and $AR_{LV}$ have exceeded $AR_{max}$. If both values do not exceed $AR_{max}$, then single ventricular pacing occurs, for example, Scenario I. If both values exceed $AR_{max}$, then bi-ventricular pacing occurs, for example, Scenario II.

Scenario I commences with a decision block 1316 that decides if $AR_{RV}$ is greater than $AR_{LV}$. If $AR_{RV}$ exceeds $AR_{LV}$, then single ventricular pacing occurs in the right ventricle (e.g., right ventricle master). If $AR_{RV}$ does not exceed $AR_{LV}$, then single ventricular pacing occurs in the left ventricle (e.g., left ventricle master).

For right ventricular pacing, the method 1300 continues in a back-up pacing block 1318 where $AV_{LV}$ is set to $AR_{LV}$ plus some back-up time (e.g., $\Delta_{BU}$). The block 1318, while optional, acts to ensure that pacing will occur in the left ventricle if no activity occurs within some given interval. The method 1300 then continues in a decision block 1320 where, if appropriate, a decision is made as to whether $\Delta_{PIVCD}$ exceeds some value ε. If the decision block 1320 decides that $\Delta_{PIVCD}$ is small, then in a set block 1324, the method 1300 sets the $AV_{RV}$ delay to $AV_{optimal}-|\Delta|$. Otherwise, the method 1300 uses $\Delta_{PIVCD}$ as a correction factor in a set block 1328, which sets $AV_{RV}$ delay to $AV_{optimal}-(|\Delta|-\Delta_{PIVCD})$.

For left ventricular pacing, the method 1300 continues in a back-up pacing block 1330 where $AV_{LV}$ is set to $AR_{LV}$ plus some back-up time (e.g., $\Delta_{BU}$). The block 1330, while optional, acts to ensure that pacing will occur in the left ventricle if no activity occurs within some given interval. The method 1300 then continues in a decision block 1332 where, if appropriate, a decision is made as to whether $\Delta_{PIVCD}$ exceeds some value ε. If the decision block 1332 decides that $\Delta_{PIVCD}$ is small, then in a set block 1336, the method 1300 sets the $AV_{LV}$ delay to $AV_{optimal}-|\Delta|$. Otherwise, the method 1300 uses $\Delta_{PIVCD}$ as a correction factor in a set block 1340, which sets $AV_{LV}$ delay to $AV_{optimal}-(|\Delta|+\Delta_{PIVCD})$.

If the decision block 1312 decides that bi-ventricular pacing is appropriate, for example, Scenario II, then the method 1300 continues in a decision block 1350, which that decides if $AR_{RV}$ is greater than $AR_{LV}$. If $AR_{RV}$ exceeds $AR_{LV}$, then bi-ventricular pacing occurs wherein the right ventricle is the master (e.g., paced prior to the left ventricle or sometimes referred to as left ventricle slave). If $AR_{RV}$ does not exceed $AR_{LV}$, then bi-ventricular pacing occurs wherein the left ventricle is the master (e.g., paced prior to the right ventricle or sometimes referred to as right ventricle slave).

For right ventricular master pacing, the method 1300 continues in a set block 1354 which sets $AV_{LV}$ to $AV_{optimal}$. A decision block 1358 follows where, if appropriate, a decision is made as to whether $\Delta_{PIVCD}$ exceeds some value ε. If the decision block 1358 decides that $\Delta_{PIVCD}$ is small, then in a set block 1362, the method 1300 sets the $AV_{RV}$ delay to $AV_{LV}-|\Delta|$. Otherwise, the method 1300 uses $\Delta_{PIVCD}$ as a correction factor in a set block 1366, which sets $AV_{RV}$ delay to $AV_{LV}-(|\Delta|-\Delta_{PIVCD})$.

For left ventricular master pacing, the method 1300 continues in a set block 1372 which sets $AV_{RV}$ to $AV_{optimal}$. A decision block 1376 follows where, if appropriate, a decision is made as to whether $\Delta_{PIVCD}$ exceeds some value ε. If the decision block 1376 decides that $\Delta_{PIVCD}$ is small, then in a set block 1380, the method 1300 sets the $AV_{LV}$ delay to $AV_{RV}-|\Delta|$. Otherwise, the method 1300 uses $\Delta_{PIVCD}$ as a correction factor in a set block 1284, which sets $AV_{LV}$ delay to $AV_{RV}-(|\Delta|+\Delta_{PIVCD})$.

If a parameter such as the aforementioned a parameter is available, then such a parameter is optionally used to further adjust and/or set one or more delays, as appropriate:

$$AV_{RV}=AV_{optimal}-\alpha|\Delta| \text{ or } PV_{RV}=PV_{optimal}-\alpha|\Delta|$$

where the term $\alpha|\Delta|$ equals or approximates $\Delta_{optimal}$. Thus, a patient's device may deliver therapy using an optimal atrio-ventricular delay in one chamber together with an optimal interventricular delay.

In instances where $\Delta_{PIVCD}$ information is available and an adjustment for interventricular conduction desirable, then the following equation may be used in Scenario I where $AR_{LV} > AR_{RV}$ (or $PR_{LV} > PR_{RV}$):

$$AV_{LV}=AV_{optimal}-\alpha(|\Delta|+\Delta_{PIVCD}) \text{ or}$$

$$PV_{LV}=PV_{optimal}-\alpha(|\Delta|+\Delta_{PIVCD})$$

Various exemplary methods, devices, systems, etc., may consider instances where normal atrio-ventricular conduction exists for one ventricle. For example, if an atrio-ventricular conduction time for the right ventricle does not exceed one or more limits representative of normal conduction, then the atrio-ventricular time for the right ventricle may serve as a basis for determining an appropriate time for delivery of stimulation to the left ventricle (or vice versa). The following equation may be used in such a situation:

$$AV_{LV} = AR_{RV} - |\Delta| \text{ or } PV_{LV} = PR_{RV} - |\Delta|$$

Figure 14:
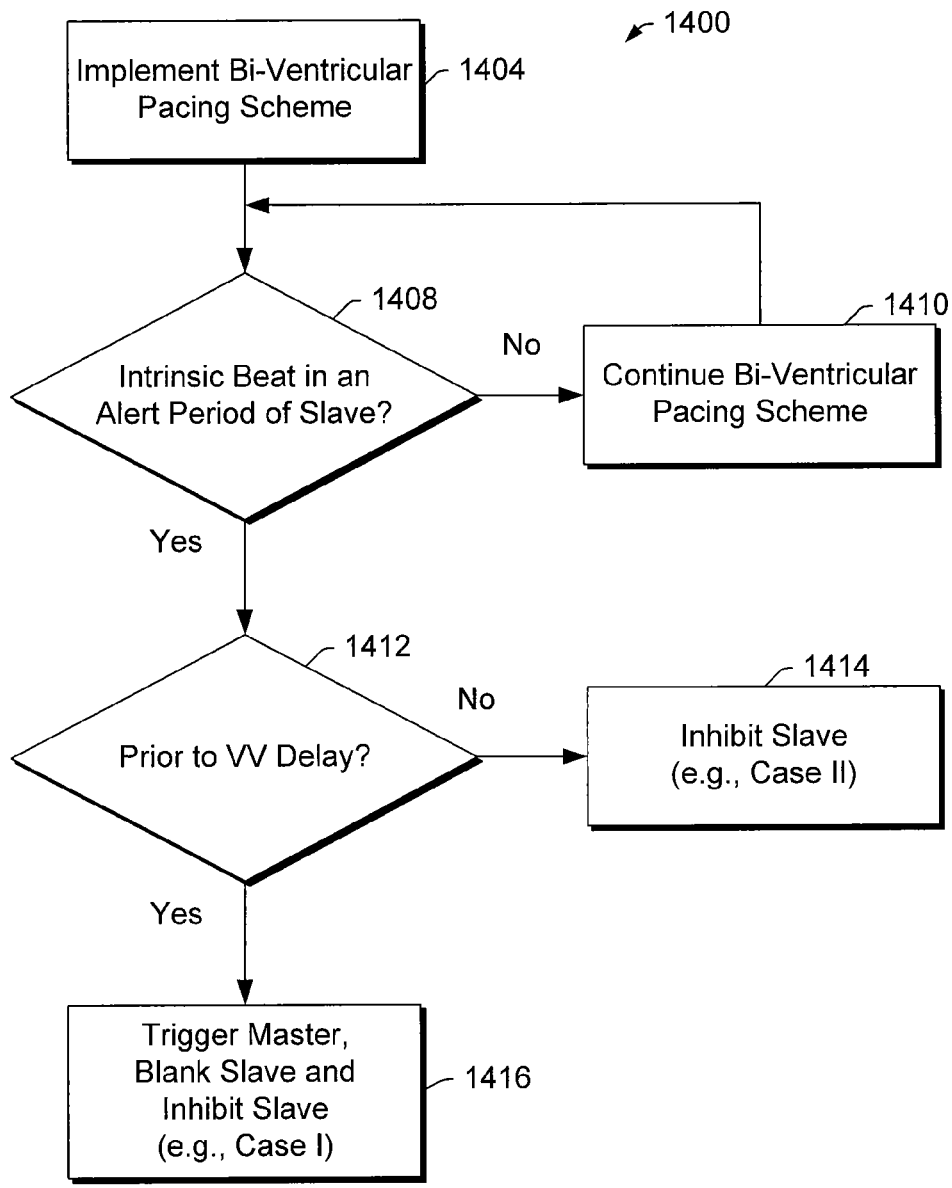
FIG. 14 is a block diagram of an exemplary method for bi-ventricular pacing.

FIG. 14 shows a block diagram of an exemplary method 1400. In an implementation block 1404, a bi-ventricular pacing scheme is implemented. A decision block 1408 follows wherein a decision is made as to whether an intrinsic event has occurred in an alert period of a ventricular channel (e.g., a slave channel). If the decision block 1408 decides that no activity or event has occurred in an alert period, then the method 1400 proceeds to a continuation block 1410 where the bi-ventricular pacing scheme continues where, as appropriate, the method 1400 flows back to the decision block (e.g., after certain programmed events, etc.). However, if the decision block 1408 decides that an intrinsic event occurred in an alert period, then another decision block 1412 follows. The decision block 1412 decides if the activity or event occurred prior to a VV delay period (e.g., a $\Delta_{programmed}$). If the decision block 1412 decides that the occurrence was not prior to a VV delay period then the method 1400 continues in an inhibition block 1414 that inhibits delivery of a pace event to a ventricle (e.g., to a slave ventricle, see Case II of FIG. 13). However, if the decision block 1412 decides that the occurrence was prior to a VV delay period then the method 1400 continues in a trigger, blank and inhibition block 1416. The trigger, blank and inhibition block 1416 acts to trigger delivery of a pace to a ventricle (e.g., a master ventricle), to initiate one or more blanking periods (e.g., atrial and/or ventricular), and to inhibit delivery of a pace to another ventricle (e.g., a slave ventricle).

Of course, an alert period for a master ventricular channel may exist wherein an intrinsic event in the master ventricle causes inhibition of a scheduled pace event in the master ventricle and causes an update in the timing of a scheduled slave pace event. For example, if an intrinsic event is sensed or detected in the master ventricle, then the VV delay may commence in response thereto. Such an exemplary method would act to preserve the VV delay (e.g., $\Delta_{programmed}$) to ensure appropriate timing of contractions in left and right ventricles.

Various exemplary methods, devices and/or systems include setting an interchamber delay between a master chamber and a slave chamber. For example, an interventricular delay may determine timing of ventricular events while an interatrial delay may determine timing of atrial events. Accordingly, an exemplary method includes setting an interchamber delay between a master chamber and a slave chamber, sensing for cardiac activity, if the sensing senses intrinsic activity in the slave chamber, determining whether the intrinsic activity occurred during the interchamber delay, and if the intrinsic activity occurred before the interchamber delay, immediately delivering stimulation to the master chamber.

With respect to the ventricles, an exemplary method includes setting an interventricular (VV) delay between a master ventricle and a slave ventricle (e.g., setting $\Delta_{programmed}$) and sensing for ventricular activity. If activity is sensed in the slave ventricle prior to the VV delay period and hence prior to delivery of a pace to the master ventricle, then immediately delivering stimulation to the master ventricle and inhibiting delivery of stimulation to the slave ventricle. If activity is sensed in the slave ventricle after delivery of stimulation to the master ventricle and prior to expiration of the VV delay, then the exemplary method may inhibit delivery of stimulation to the slave ventricle. Such a method optionally includes adjusting the ventricular refractory period in the slave ventricle channel to be greater than the appropriate PIVCD minus VV. PIVCD could be either PIVCD-LR or PIVCD-RL or average of the two.

An exemplary implantable device includes a power supply, a processor, a lead including one or more electrodes capable of being positioned proximate to a master ventricle, a lead including one or more electrodes capable of being positioned proximate to a slave ventricle, and control logic, executable through use of the processor, to set an interventricular delay between the master ventricle and the slave ventricle and to call for immediate delivery of stimulation to the master ventricle using the lead proximate to the master ventricle upon detection of intrinsic activity in the slave ventricle prior to the interventricular delay (e.g., prior to delivery of stimulation to the master ventricle). Such control logic optionally inhibits delivery of stimulation to the slave ventricle.

Various exemplary methods, devices and/or systems may consider instances where normal atrio-ventricular conduction exists for one ventricle. For example, if an atrio-ventricular conduction time for the right ventricle does not exceed one or more limits representative of normal conduction, then the atrio-ventricular time for the right ventricle may serve as a basis for determining an appropriate time for delivery of stimulation to the left ventricle (or vice versa). The following equation may be used in such a situation:

$$AV_{LV} = AR_{RV} - |\Delta| \text{ or } PV_{LV} = PR_{RV} - |\Delta|$$

With respect to backup pulses, a backup pulse (e.g., for purposes of safety, etc.) may be set according to the following equation:

$$AV_{RV} = AR_{RV} + |\gamma| \text{ or } PV_{RV} = PR_{RV} + |\gamma|$$

Of course, administration of a backup pulse may occur upon one or more conditions, for example, failure to detect activity in the particular ventricle within a given period of time. The parameter $\gamma$ is a short time delay, for example, of approximately 5 ms to approximately 10 ms.

According to the equation for $AV_{LV}$, there may not be an a priori need for a particular $AV_{optimal}$ or $PV_{optimal}$. Instead, a need may exist for one or more limits to determine if a sensed AR or PR may be considered normal or acceptable. Further, in such exemplary methods, devices and/or systems, an alert period may be implemented wherein sensing or detection of an intrinsic event in a channel associated with the scheduled pace event causes inhibition of the pace event. For example, if an alert period exist prior to the scheduled pace event and intrinsic activity is detected then inhibition of the pace event may occur, which may act to conserve energy of an implanted device. However, if the alert period expires without sensing or detecting intrinsic activity, the back up pacing pulse in the right ventricle is delivered at $AV_{RV}$ and $AV_{LV}$ will be kept scheduled.

In many instances, heart condition will affect $AR_{RV}$ and $AR_{LV}$, and PIVCD, which, in turn, may affect an existing optimal VV delay setting. Various exemplary methods, devices and/or systems include triggering of an algorithm to update an existing optimal VV delay according to a predetermined time or event period or activity sensors for exercise, resting, etc. An exemplary device may include a learning method that learns based on differences in conduction times (e.g., $AR_{RV}$ and $AR_{LV}$, PIVCD, etc.) such that parameters associated with different heart demands can be stored. The exemplary learning method may then extract such learned or other parameters to set an optimal VV delay.

In the aforementioned learning example, if the device learns on the basis of different cardiac demands, the device may adjust AV delay and/or VV delay and/or learn a new AV delay and/or VV delay upon a change in cardiac demand. According to this example, use of external measurement or sensing equipment (e.g., echocardiogram, etc.) is optional. Further, use of internal measurement or sensing equipment for sensing pressure or other indicators of hemodynamic performance is optional. Again, adjustment and learning may rely on IEGM information and/or cardiac other rhythm information.

An exemplary method relies on an atrial to right ventricular conduction time, an atrial to left ventricular conduction time and a α parameter, for example, as described above, to determine an optimal AV delay and/or VV delay. Another exemplary method relies on an atrial to right ventricular conduction time, an atrial to left ventricular conduction time and a limit that may be used to decide whether one or more of the conduction times are acceptable. In these examples, an interventricular conduction time may be used in lieu of an atrial to ventricular conduction time, for example, where ventricular activity originates with a common atrial event.

According to various exemplary methods, devices and/or systems, information acquired (e.g., sensed, detected and/or determined) may be used to diagnose cardiac condition. For example, an exemplary method may track AV delays and/or VV delays over time. Such information may then be used to determine subsequent therapy.

Various exemplary methods, devices and/or systems include determining an optimal interventricular delay (e.g., $\Delta_{optimal}$) using a modality such as an echocardiogram. While an internal echocardiogram or implantable hemodynamic sensors may be available or become available and be able to measure such optimal delays for a variety of patient circumstances (e.g., sleep, exercise, etc.), an exemplary method, device and/or system includes use of internal sensors to measure and/or update such an optimal delay and/or to determine values for one or more parameters related to an optimal delay. For example, a blood pressure sensor (e.g., aortic arch, etc.) may be used to determine or to update an optimal delay. Further, information may be collected over a period of time to determine heart condition (e.g., deterioration, improvement, etc.).

In general, an optimal interventricular delay will change as demand and/or heart conditions change. Thus, an exemplary method may determine an optimal interventricular delay during sleep on a nightly, a weekly or some other basis. Such an exemplary method may determine an optimal interventricular delay within a matter of minutes (e.g., approximately 5 heart beats). Such an exemplary method may be triggered according to a change in heart rate or some other parameter related to heart condition. Over time or at time of programming, an exemplary device may store one or more optimal interventricular delays as a function of heart rate, heart condition, etc., and then implement a selected delay from the stored delays upon occurrence of a rate, condition, etc., or a change in rate, condition, etc. Such dynamic control of interventricular delay can improve cardiac performance and potentially allow for an improvement in patient quality of life (e.g., allow for a broader range of patient activity). If after some predetermined period of time or upon occurrence of a particular condition, an exemplary device may indicate a need for a more rigorous determination, for example, via an echocardiogram.

An exemplary method includes monitoring fluid status and assessing cardiac condition based on fluid status and heart sound information. For example, fluid status may be "dry" or "wet" and the S3 heart sound may appear when the fluid status is "wet". Accordingly, vibration information may be linked to fluid status and optionally used to adjust one or more pacing parameters. Such information may also be used to monitor heart condition.

An exemplary method performs an optimization for AV and W delays, implements optimal delays and then determines if vibration information indicates presence of significant S3 heart sound energy. If the method detects no significant S3 heart sound energy, then the method continues by delivering pacing using the optimized delays. Otherwise, the method may issue an alert or take other action.

Figure 15:
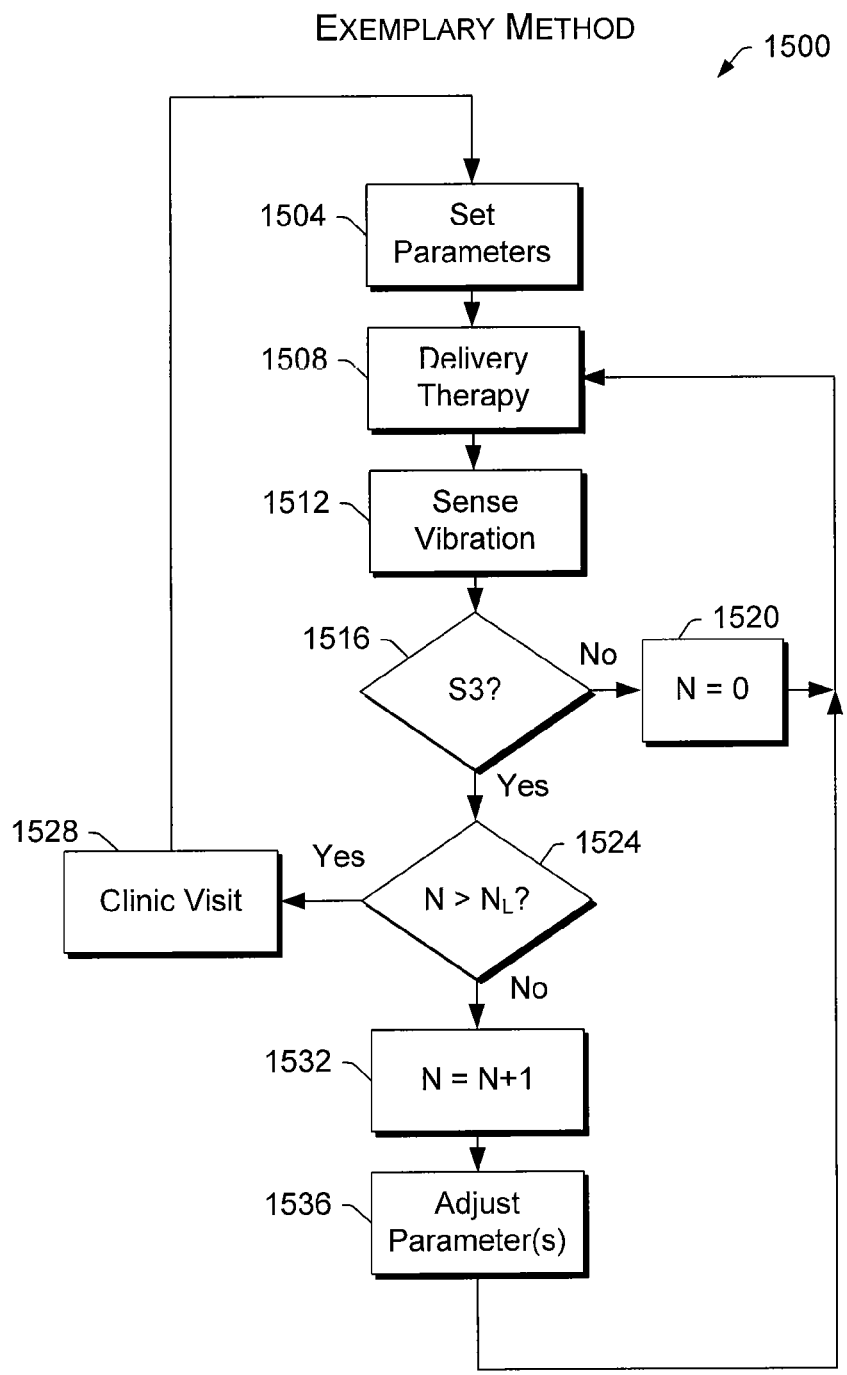
FIG. 15 is a block diagram of an exemplary method for sensing vibration and optionally adjusting one or more parameters associated with a pacing therapy or optionally issuing an alert.

An exemplary method implements an optimization algorithm for AV and VV delays in response to detection of significant S3 heart sound energy. Such a method can also implement optimized AV and VV delays and then check to see if the energy diminished, which can indicate that a patient experienced some hemodynamic benefit from the optimized AV and VV delays. An exemplary technique optionally uses FIG. 15 shows an exemplary method 1500 for adjusting one or more pacing parameters based at least in part on sensing vibrations associated with left ventricular filling. The method 1500 commences in a set block 1504 where pacing therapy parameters are set by an implantable device or by a programmer in communication with an implantable device (e.g., during a clinic visit or via a networked-based consultation). The set block 1504 may use the method 1300 or other method for setting the pacing therapy parameters.

A delivery block 1508 calls for delivery of the pacing therapy using the set parameters. For example, where the pacing therapy includes bi-ventricular pacing, the parameters may control various intervals such as AV/PV interval and VV interval (or AV/PV$_{RV}$ and AV/PV$_{LV}$). A sense block 1512 calls for sensing at least vibration associated with left ventricular filling. The sense block 1512 may call for such sensing on a beat-by-beat or other basis.

A decision block 1516 may operate during sensing or after sensing. The decision block 1516 decides if S3 exists, for example, if vibration associated with left ventricular filling has certain features or characteristics associated with dysfunction or asynchrony. Features may include amplitude above a limit, duration, timing with respect to other events, etc. If the decision block 1516 decides that S3 does not exist (according to one or more criteria), then the method 1500 enters a counter block 1520 that sets a counter "N" to zero or some other base value. The method 1500 then continues at the delivery block 1508 to deliver the pacing therapy using the set parameters, per the set block 1504.

If the decision block 1516 decides that S3 exists (according to one or more criteria), then the method 1500 enters another decision block 1524 that decides if the counter "N" has exceeded a counter limit "$N_L$". If the decision block 1524 decides that the counter N has exceeded the counter limit $N_L$, then the method 1500 enters an alert block 1528 that alerts a patient or a clinician that an issue exists with the pacing therapy with respect to left ventricular filling. The alert block 1528 may call for a clinic visit or a network-based intervention (e.g., Internet, telephone, etc.) to further investigate the issue.

If the decision block 1524 decides that the counter N has not exceeded the counter limit $N_L$, then the method 1500 enters an increment block 1532 that increments the counter N and an adjustment block 1536 that adjusts one or more parameters of a pacing therapy in an attempt to improve cardiac performance and hence diminish or eliminate occurrence of S3. The adjustment block 1536 optionally selects a different therapy which may use one or more different parameters. The adjustment block 1536 may use sensed vibration information in making an adjustment or selection. After the adjustment block 1536, the method 1500 continues at the delivery block 1508 which calls for delivery of therapy according to one or more adjusted parameters or according to a new therapy, based on appropriate parameters.

As described above, the exemplary method 1500 can automatically, based at least in part on sensed vibration associated with left ventricular filling, call for adjustment to one or more pacing therapy parameters, call for selection of a different pacing therapy, or issue an alert.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc. Various methods may be implemented, in whole or in part, by computer-executable instructions. Such instructions may be stored on one or more computer-readable media.

The invention claimed is:

1. A method comprising:
   measuring one or more cardiac electrocardiogram signals;
   sensing a vibration signal from an intrathoracic vibration sensor while receiving the electrocardiogram cardiac signals;
   processing the measured cardiac electrocardiogram signals to determine one or more optimized bi-ventricular pacing parameters;
   delivering bi-ventricular pacing pulses in accordance with the optimized pacing parameters;
   analyzing one or more features of the sensed vibration signal to detect a S3 heart sound while delivering bi-ventricular pacing pulses in accordance with the optimized pacing parameters; and
   adjusting one or more of the optimized bi-ventricular pacing parameters in response to the detection of the S3 heart sound.

2. The method of claim 1 wherein the adjustment adjusts an atrio-ventricular delay.

3. The method of claim 1 wherein the adjustment adjusts an interventricular delay.

4. The method of claim 1 wherein the deciding calls for the adjustment if the amplitude of the vibration signal exceeds the amplitude limit.

5. The method of claim 1 wherein the analyzing determines if an audible third heart sound exists.

6. The method of claim 1 wherein the intrathoracic vibration sensor comprises a MEMS accelerometer.

7. The method of claim 1 wherein the analyzing further comprises analyzing the vibration signal associated with opening of the mitral valve.

8. The method of claim 1 wherein the analyzing comprises comparing the vibration signal to one or more criteria derived from echocardiography E waves.

9. The method of claim 1 further comprising receiving a second vibration signal from another intrathoracic vibration sensor.

10. The method of claim 1 wherein the intrathoracic vibration sensor comprises a sensor positioned proximate to the left ventricle of the heart.

11. The method of claim 1 wherein the adjustment comprises use of a paced interventricular conduction delay.

12. The method of claim 1 further comprising repeating the analyzing and deciding and issuing an alert if the deciding calls for a predetermined number of successive adjustments.

13. An implantable system comprising an:
   an implantable cardiac resynchronization therapy (CRT) device coupled to one or more leads having one or more electrodes and at least one lead based vibration sensor, the CRT device comprising
   memory configured to store a baseline vibration signal;
   a processor;
   one or more pulse generators coupled to the one or more leads and the processor;
   the processor having control logic configured to receive electrocardiogram signals from the one or more electrodes and to process the measured electrocardiogram signals to derive one or more optimized pacing parameters and to control the delivery of bi-ventricular pacing pulses by the one or more pulse generators in accordance with the optimized pacing parameters, the control logic being further configure to receive a vibration signal from the vibration sensor and to analyze one or more features of the vibration signal to detect a S3 heart sound while delivering bi-ventricular pacing pulses in accordance with the optimized pacing parameters, wherein the control logic is configured to adjust one or more parameters of a cardiac resynchronization therapy (CRT) in response to the detection of the heart sound.

14. The device of claim 13 further comprising control logic to issue an alert based at least in part on the vibration signal wherein the alert pertains to the CRT.

15. The device of claim 13 wherein the vibration sensor comprises a MEMS microphone.

16. The device of claim 13 wherein the vibration sensor comprises a strain gauge.

* * * * *